(12) United States Patent
Huang et al.

(10) Patent No.: US 11,466,025 B2
(45) Date of Patent: Oct. 11, 2022

(54) THIENOPYRIDINE DERIVATIVES CONTAINING UNSATURATED ALIPHATIC OLEFINIC BOND, PREPARATION METHOD AND USE THEREOF

(71) Applicant: Tianjin Institute of Pharmaceutical Research Co., Ltd., Tianjin (CN)

(72) Inventors: Changjiang Huang, Tianjin (CN); Shijun Zhang, Tianjin (CN); Lingjun Li, Tianjin (CN); Lei Liu, Tianjin (CN); Yuquan Li, Tianjin (CN); Jing Yuan, Tianjin (CN); Hui Yan, Tianjin (CN); Songhui Wang, Tianjin (CN); Xuemin Zheng, Tianjin (CN); Qunchao Wei, Tianjin (CN); Xuyuan Liu, Tianjin (CN); Wei Wei, Tianjin (CN); Weiren Xu, Tianjin (CN); Lida Tang, Tianjin (CN); Meixiang Zou, Tianjin (CN)

(73) Assignee: TIANJIN INSTITUTE OF PHARMACEUTICAL RESEARCH CO., LTD., Tianjin (CN)

( * ) Notice: Subject to any disclaimer, the term of this patent is extended or adjusted under 35 U.S.C. 154(b) by 468 days.

(21) Appl. No.: 16/640,612

(22) PCT Filed: Aug. 22, 2018

(86) PCT No.: PCT/CN2018/101729
§ 371 (c)(1),
(2) Date: Feb. 20, 2020

(87) PCT Pub. No.: WO2019/037740
PCT Pub. Date: Feb. 28, 2019

(65) Prior Publication Data
US 2020/0361952 A1    Nov. 19, 2020

(30) Foreign Application Priority Data
Aug. 24, 2017 (CN) .......................... 201710735303.1

(51) Int. Cl.
| C07D 495/04 | (2006.01) |
| A61P 7/02 | (2006.01) |
| A61P 9/10 | (2006.01) |
| A61K 31/4365 | (2006.01) |

(52) U.S. Cl.
CPC .............. *C07D 495/04* (2013.01); *A61P 7/02* (2018.01); *C07B 2200/13* (2013.01)

(58) Field of Classification Search
CPC . C07D 495/04; A61P 7/02; A61P 9/10; C07B 2200/13; A61K 31/4365
See application file for complete search history.

(56) References Cited

FOREIGN PATENT DOCUMENTS

| CN | 102199163 A | 8/2011 | |
| CN | 103254211 A | 8/2013 | |
| CN | 103554132 A | 2/2014 | |
| EP | 2947475 A1 | 9/2012 | |
| EP | 3290423 B1 * | 7/2021 | ......... A61K 31/4365 |
| JP | 2013518825 A | 5/2013 | |
| WO | 2008/060934 A2 | 5/2008 | |
| WO | 2011/095049 A1 | 8/2011 | |
| WO | 2014/059884 A1 | 4/2014 | |

OTHER PUBLICATIONS

State Intellectual Property Office of the P.R. China, International Search Report (with English translation) issued in International Application No. PCT/CN2018/101729, dated Nov. 8, 2018, 6 pages.
State Intellectual Property Office of the P.R. China, Written Opinion of the International Searching Authority (with English translation) issued in International Application No. PCT/CN2018/101729, dated Nov. 8, 2018, 6 pages.
The International Bureau of WIPO, International Preliminary Report on Patentability issued in International Application No. PCT/CN2018/101729, dated Feb. 25, 2020, 4 pages.
Japan Patent Office, Office Action (with English translation) issued in corresponding Japanese Patent Application No. 2020-531805, dated Apr. 28, 2021, 11 pages.
Korean Intellectual Property Office, Office Action (with English translation) issued in corresponding Korean Patent Application No. 10-2020-7008499, dated Jun. 21, 2021, 13 pages.
Hirayama, "Principle of crystallization," The Organize Compound Crystal Production Handbook, (with English translation) 2008, pp. 17-23, 37, 40, 45-51 and 57.
Kawaguchi, Y., et al. "Drug and crystal polymorphism," Journal of Human Environmental Engineering, (with English translation, 2002, vol. 4, No. 2, pp. 1-9.

* cited by examiner

*Primary Examiner* — John M Mauro
(74) *Attorney, Agent, or Firm* — Christensen O'Connor Johnson Kindness PLLC

(57) ABSTRACT

The present invention provides a compound having a structure of formula (I), a preparation method and use thereof, and a pharmaceutical composition containing the compound, wherein R is methyl, ethyl, propyl, vinyl or propenyl. The present invention also provides a crystalline form of the compound, a preparation method and use of the crystalline form, and a pharmaceutical composition comprising the crystalline form. The compounds having the structure of formula (I) of the present invention are present in a solid form, which not only can solve the problem of clopidogrel resistance, but also can solve the problem of severe hemorrhagic side effect and poor safety of some drugs, as well as the problem of poor stability of existing compounds. It can be developed into an ADP receptor antagonist antiplatelet agent with clear therapeutic effect, no resistance and better stability.

(I)

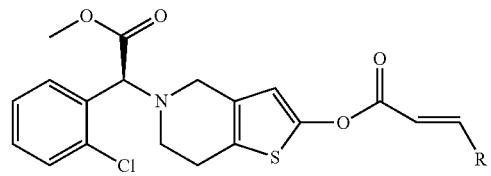

37 Claims, 12 Drawing Sheets

THIENOPYRIDINE DERIVATIVES CONTAINING UNSATURATED ALIPHATIC OLEFINIC BOND, PREPARATION METHOD AND USE THEREOF

TECHNICAL FIELD

The present invention belongs to the field of medical technology. Specifically, the present invention relates to a class of compounds having an anti-platelet aggregation effect, a preparation method and use thereof, as well as a pharmaceutical composition containing the compound. More specifically, the present invention relates to a thienopyridine derivative containing an unsaturated aliphatic olefinic bond, a preparation method and use thereof, as well as a pharmaceutical composition. The present invention also relates to a crystalline form of the compound, a preparation method and use of the crystalline form, and a pharmaceutical composition comprising the crystalline form.

BACKGROUND ART

Clopidogrel is an oral ADP receptor antagonist jointly developed by two pharmaceutical companies, Sanofi and Bristol-Myers Squibb, which has been approved for marketing. It is developed on the basis of certain structural modifications to the early-developed antiplatelet agent, ticlopidine, and is currently used as a first-line antithrombotic agent clinically. However, it has been confirmed in many years of clinical use that clopidogrel has great defects. As a prodrug, clopidogrel needs to be subjected to two steps of metabolism in vivo by the P450 enzyme system in the liver, and metabolized into an active metabolite to take effect. As there are differences in the expression of related enzymes in different individuals, especially CYP2C19, on which the metabolism of the first step depends, has gene polymorphism, leading to large individual differences between clinical treatment effects of clopidogrel, and it is prone to make the phenomenon of "clopidogrel resistance" happen, which would further lead to somewhat harmful cardiovascular events.

Prasugrel was jointly developed by Daiichi Sankyo (Japan) and Eli Lilly (US), which is an ADP receptor antagonist antiplatelet agent developed on the basis of clopidogrel. In comparison with clopidogrel, prasugrel takes effect more rapidly and has greater activity, with less difference in response to the drug between patients. However, prasugrel also has great defects. It has a greater and even fatal hemorrhagic risk, and also has adverse effects such as hepatotoxicity thrombocytopenia, and neutropenia.

At the same time, thienopyridine compounds reported in the existing literatures also have the problem of instability. By way of example, clopidogrel free base is an oil, which has many disadvantages such as being unstable and difficult to be made into oral preparations. Other thienopyridine compounds reported in some literatures have similar disadvantages that the compounds are present as oils and need to form salts with strong acids such as hydrochloric acid and sulfuric acid, and the product is unstable and prone to degradation. These disadvantages make these compounds have poor druggability, or be prone to have problems during production, sale, storage, and use.

So far, no research has shown that there is a compound which can solve both the problem of clopidogrel resistance and the problem of severe hemorrhagic side effect and potential hepatotoxicity of prasugrel, and can also solve the problem of poor stability.

Therefore, there is an urgent clinical need to develop ADP receptor antagonist antiplatelet agents with clear therapeutic effect, no metabolic resistance, higher safety and better stability.

DESCRIPTION OF THE INVENTION

The technical problem to be solved by the present invention is to overcome the above-mentioned disadvantages and develop an ADP receptor antagonist antiplatelet agent with clear therapeutic effect, no resistance, as well as higher safety and stability.

It is an object of the present invention to provide a thienopyridine ester derivative containing an unsaturated aliphatic olefinic bond, a method for preparing the thienopyridine ester derivative containing an unsaturated aliphatic olefinic bond, use of the thienopyridine ester derivative containing an unsaturated aliphatic olefinic bond, and a pharmaceutical composition comprising the thienopyridine ester derivative containing an unsaturated aliphatic olefinic bond.

It is another object of the present invention to provide a crystalline form of the thienopyridine ester derivative containing an unsaturated aliphatic olefinic bond, a method for preparing the crystalline form, a pharmaceutical composition comprising the crystalline form, and use of the crystalline form.

It is yet another object of the present invention to provide a method for preventing and/or treating cardiovascular and cerebrovascular diseases caused by platelet aggregation.

The object of the present invention is achieved by the following technical solutions:

In one aspect, the present invention provides a compound having a structure of formula (I):

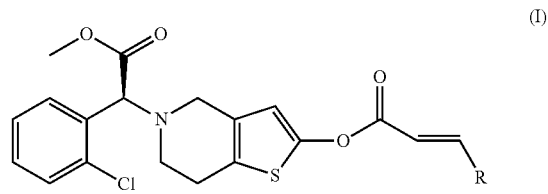

wherein R is methyl, ethyl, propyl, vinyl or propenyl.

The compound having the structure of formula (I) of the present invention is preferably selected from the following compounds:

I-1: methyl (S,E)-2-(2-chlorophenyl)-2-(2-(2-butenoyloxy)-6,7-dihydrothieno[3,2-c]pyridin-5(4H)-yl)-acetate

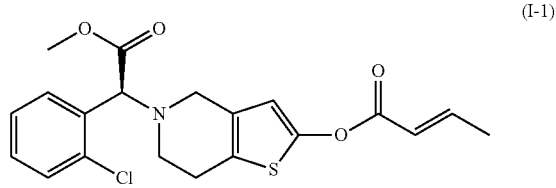 [SMILES: C/C=C/C(=O)Oc1cc2c(s1)CCN([C@H](C(=O)OC)c1ccccc1Cl)C2]

I-2: methyl (S)-2-(2-chlorophenyl)-2-(2-((2E,4E)-2,4-hexadienoyloxy)-6,7-dihydrothieno[3,2-c]pyridin-5(4H)-yl)-acetate (I-2)

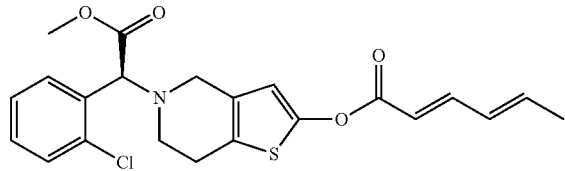 [SMILES: C/C=C/C=C/C(=O)Oc1cc2c(s1)CCN([C@H](C(=O)OC)c1ccccc1Cl)C2]

I-3: methyl (S,E)-2-(2-chlorophenyl)-2-(2-(2,4-pentadienoyloxy)-6,7-dihydrothieno[3,2-c]pyridin-5(4H)-yl)-acetate (I-3)

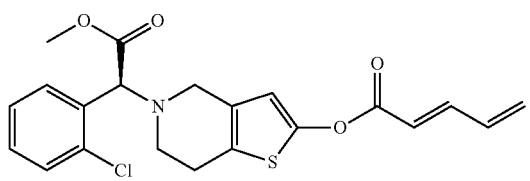 [SMILES: C=C/C=C/C(=O)Oc1cc2c(s1)CCN([C@H](C(=O)OC)c1ccccc1Cl)C2]

I-4: methyl (S,E)-2-(2-chlorophenyl)-2-(2-(2-pentenoyloxy)-6,7-dihydrothieno[3,2-c]pyridin-5(4H)-yl)-acetate (I-4)

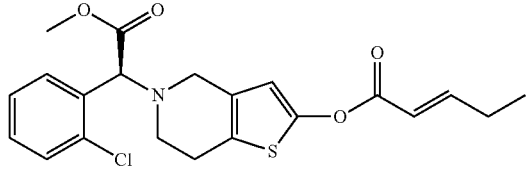

I-5: methyl (S,E)-2-(2-chlorophenyl)-2-(2-(2-hexenoyloxy)-6,7-dihydrothieno[3,2-c]pyridin-5(4H)-yl)-acetate (I-5)

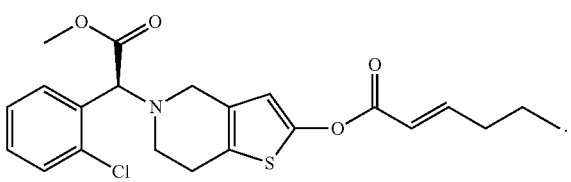

The compound having the structure of formula (I) of the present invention is more preferably selected from the following compounds:

I-1: methyl (S,E)-2-(2-chlorophenyl)-2-(2-(2-butenoyloxy)-6,7-dihydrothieno[3,2-c]pyridin-5(4H)-yl)-acetate; and I-2: methyl (S)-2-(2-chlorophenyl)-2-(2-((2E,4E)-2,4-hexadienoyloxy)-6,7-dihydrothieno[3,2-c]pyridin-5(4H)-yl)-acetate.

In another aspect, the present invention provides a method for preparing the compound having the structure of formula (I) of the present invention, the method comprises the steps of:

reacting a compound having a structure of formula (II) with a corresponding acid, acyl chloride or acid anhydride in the presence of a base to prepare the compound having the structure of formula (I):

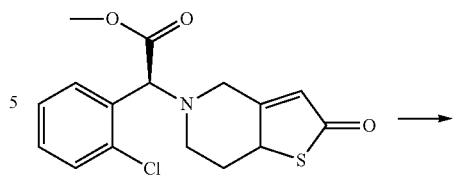

(II)

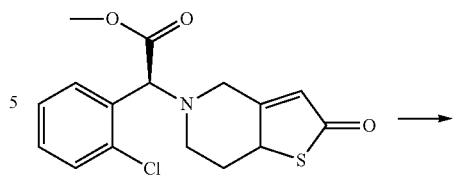

(I)

wherein R is methyl, ethyl, propyl, vinyl or propenyl;

preferably, in the method for preparing the compound having the structure of formula (I) of the present invention, the base is triethylamine or N,N-diisopropylethylamine, and/or the reaction is carried out in the presence of a solvent such as dichloromethane.

preferably, the compound having the structure of formula (II) is prepared by reacting a compound having a structure of formula (III) with a compound having a structure of formula (IV) in the presence of a base:

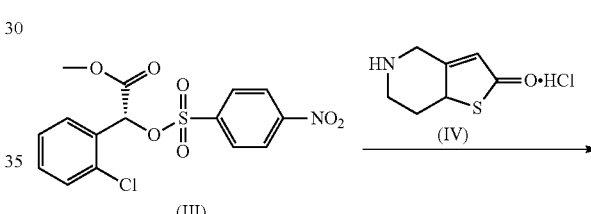

(III)     (IV)

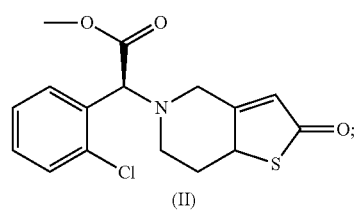

(II)

preferably, in the reaction for preparing the compound having the structure of formula (II) from the compound having the structure of formula (III) and the compound having the structure of formula (IV), said base is potassium carbonate, said reaction is carried out in the presence of a solvent such as acetonitrile, and/or said reaction is carried out at a temperature of 20-40° C.

In some embodiments, the solvent used in the preparation method of the present invention may be a solvent which is inert under the reaction conditions, including, but not limited to, ethers, such as tetrahydrofuran, diethyl ether, ethylene glycol dimethyl ether etc.; halogenated hydrocarbons, such as 1,2-dichloroethane, dichloromethane, chloroform, carbon tetrachloride etc.; alcohols, such as methanol, ethanol, isopropanol, tert-butanol etc.; hydrocarbons, such as benzene, toluene, xylene, hexane, cyclohexane etc.; and other solvents, such as dimethyl sulfoxide, dimethylformamide, acetonitrile, pyridine, water, hexamethylphosphoric triamide etc. The solvent may also be a mixture of the above solvents.

In certain embodiments of the present invention, in the method for preparing the compound having the structure of formula (I) of the present invention and in the reaction for preparing the compound having the structure of formula (II) from the compound having the structure of formula (I) and the compound having the structure of formula (IV), the reaction can be carried out under different pressures, such as a reduced pressure, a normal pressure or an increased pressure, preferably under a normal pressure.

In certain embodiments of the present invention, in the method for preparing the compound having the structure of formula (I) of the present invention and in the reaction for preparing the compound having the structure of formula (II) from the compound having the structure of formula (I) and the compound having the structure of formula (IV), the reaction is generally carried out at a temperature of −78° C. to a reflux temperature, preferably in a range of 0° C. to a reflux temperature.

In yet another aspect, the present invention provides use of the compound having the structure of formula (I) of the present invention in the manufacture of a medicament for preventing and/or treating cardiovascular and cerebrovascular diseases caused by platelet aggregation, and the cardiovascular and cerebrovascular diseases are, for example, coronary artery syndrome, myocardial infarction, myocardial ischemia, and the like.

In another aspect, the present invention provides a method for preventing and/or treating cardiovascular and cerebrovascular diseases caused by platelet aggregation, the method comprises administering to a subject in need thereof a therapeutically effective amount of the compound having the structure of formula (I) of the present invention, the cardiovascular and cerebrovascular diseases are, for example, coronary artery syndrome, myocardial infarction, myocardial ischemia, and the like.

In yet another aspect, the present invention provides a pharmaceutical composition comprising the compound having the structure of formula (I) of the present invention and a pharmaceutically acceptable carrier or excipient.

In certain embodiments of the present invention, the pharmaceutical composition is a solid oral preparation, a liquid oral preparation, or an injection. Preferably, the solid oral preparation is a tablet, a capsule or a granule; the liquid oral preparation is a syrup or an oral solution; and/or the injection is a liquid injection, a powder for injection or a small-volume infusion solution.

In another aspect, the present invention also provides a crystalline form A of methyl (S,E)-2-(2-chlorophenyl)-2-(2-(2-butenoyloxy)-6,7-dihydrothieno[3,2-c]pyridin-5(4H)-yl)-acetate (I-1), a preparation method and use thereof, as well as a pharmaceutical composition comprising the crystalline form A.

The crystalline form A of methyl (S,E)-2-(2-chlorophenyl)-2-(2-(2-butenoyloxy)-6,7-dihydrothieno[3,2-c]pyridin-5(4H)-yl)-acetate (I-1) has an X-ray powder diffraction pattern having diffraction peaks at 5.31, 16.13, 20.24 and 21.58 expressed by 2θ degree using Cu-Ka radiation, with a 2θ angle measurement error being ±0.2.

Preferably, the crystalline form A of methyl (S,E)-2-(2-chlorophenyl)-2-(2-(2-butenoyloxy)-6,7-dihydrothieno[3,2-c]pyridin-5(4H)-yl)-acetate (I-1) has an X-ray powder diffraction pattern having diffraction peaks at 5.31, 10.70, 12.43, 16.13, 17.47, 20.24, 21.58, 25.83 and 27.09 expressed by 2θ degree using Cu-Ka radiation, with a 2θ angle measurement error being ±0.2.

Preferably, the crystalline form A of methyl (S,E)-2-(2-chlorophenyl)-2-(2-(2-butenoyloxy)-6,7-dihydrothieno[3,2-c]pyridin-5(4H)-yl)-acetate (I-1) has an X-ray powder diffraction pattern having a diffraction angle (2θ) and interplanar spacing (d value) as shown in Table 1, with the 2θ angle measurement error being ±0.2.

TABLE 1

| Diffraction angle and interplanar spacing results of X-ray powder diffraction pattern of crystalline form | |
|---|---|
| 2θ (±0.2°) | d (Å) |
| 5.31 | 16.63 |
| 10.70 | 8.26 |
| 12.43 | 7.12 |
| 16.13 | 5.49 |
| 17.47 | 5.07 |
| 20.24 | 4.38 |
| 21.58 | 4.11 |
| 25.83 | 3.45 |
| 27.09 | 3.29 |

Preferably, the crystalline form A of methyl (S,E)-2-(2-chlorophenyl)-2-(2-(2-butenoyloxy)-6,7-dihydrothieno[3,2-c]pyridin-5(4H)-yl)-acetate (I-1) has an X-ray powder diffraction pattern substantially as shown in FIG. 1.

Preferably, the crystalline form A of methyl (S,E)-2-(2-chlorophenyl)-2-(2-(2-butenoyloxy)-6,7-dihydrothieno[3,2-c]pyridin-5(4H)-yl)-acetate (I-1) has a DSC-TGA pattern substantially as shown in FIG. 2.

The crystalline form A of methyl (S,E)-2-(2-chlorophenyl)-2-(2-(2-butenoyloxy)-6,7-dihydrothieno[3,2-c]pyridin-5(4H)-yl)-acetate (I-1) of the present invention has good appearance stability and reproducibility between batches, which exists as a white or off-white solid and is stable as crystalline form A during continuous preparation of multiple batches.

The crystalline form A of methyl (S,E)-2-(2-chlorophenyl)-2-(2-(2-butenoyloxy)-6,7-dihydrothieno[3,2-c]pyridin-5(4H)-yl)-acetate (I-1) of the present invention has a good stability, and the crystalline form remains stable under high temperature, high humidity, and light conditions.

The present invention also provides a method for preparing the crystalline form A of methyl (S,E)-2-(2-chlorophenyl)-2-(2-(2-butenoyloxy)-6,7-dihydrothieno[3,2-c]pyridin-5(4H)-yl)-acetate (I-1), comprising the steps of:
dissolving the compound of methyl (S,E)-2-(2-chlorophenyl)-2-(2-(2-butenoyloxy)-6,7-dihydrothieno[3,2-c]pyridin-5(4H)-yl)-acetate (I-1) in an organic solvent, heating to obtain a clear solution, precipitating a crystal by stirring and cooling, collecting the crystal by filtration, and drying to obtain the crystalline form A of methyl (S,E)-2-(2-chlorophenyl)-2-(2-(2-butenoyloxy)-6,7-dihydrothieno[3,2-c]pyridin-5(4H)-yl)-acetate (I-1), wherein the organic solvent is one or more selected from the group consisting of methanol, ethanol, propanol, isopropanol, toluene, ethyl acetate, acetone, acetonitrile and methyl tert-butyl ether.

Preferably, in the method of the present invention for preparing the crystalline form A of methyl (S,E)-2-(2-chlorophenyl)-2-(2-(2-butenoyloxy)-6,7-dihydrothieno[3,2-c]pyridin-5(4H)-yl)-acetate (I-1), the step of heating comprises heating to a reflux temperature; and/or the step of precipitating a crystal by cooling comprises cooling to a temperature of 10-30° C.

The present invention also provides use of the crystalline form A of methyl (S,E)-2-(2-chlorophenyl)-2-(2-2-butenoyloxy)-6,7-dihydrothieno[3,2-c]pyridin-5 (4H)-yl)-acetate (I-1) in the manufacture of a medicament for preventing and/or treating cardiovascular and cerebrovascular diseases caused by platelet aggregation, and the cardiovascular and cerebrovascular diseases are, for example, coronary artery syndrome, myocardial infarction, myocardial ischemia, and the like.

The present invention also provides a method for preventing and/or treating cardiovascular and cerebrovascular diseases caused by platelet aggregation, the method comprises administering to a subject in need thereof a therapeutically effective amount of the crystalline form A of methyl (S,E)-2-(2-chlorophenyl)-2-(2-(2-butenoyloxy)-6,7-dihydrothieno[3,2-c]pyridin-5(4H)-yl)-acetate (I-1), and the cardiovascular and cerebrovascular diseases are, for example, coronary artery syndrome, myocardial infarction, myocardial ischemia, and the like.

The present invention also provides a pharmaceutical composition comprising the crystalline form A of methyl (S,E)-2-(2-chlorophenyl)-2-(2-(2-butenoyloxy)-6,7-dihydrothieno[3,2-c]pyridin-5(4H)-yl)-acetate (I-1) and a pharmaceutically acceptable carrier or excipient.

In certain embodiments of the present invention, the pharmaceutical composition is a solid oral preparation, a liquid oral preparation, or an injection; preferably, the solid oral preparation is a tablet, a capsule or a granule; the liquid oral preparation is a syrup or an oral solution; and/or the injection is a liquid injection, a powder for injection or a small-volume infusion solution.

In another aspect, the present invention also provides a crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), a preparation method and use thereof, as well as a pharmaceutical composition comprising the crystalline form A.

The crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has an X-ray powder diffraction pattern having diffraction peaks at 5.52, 16.73, 19.43 and 22.38 expressed by 2θ degree using Cu-Kα radiation, with a 2θ angle measurement error being ±0.2.

Preferably, the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has an X-ray powder diffraction pattern having diffraction peaks at 5.52, 11.10, 12.30, 16.73, 18.86, 19.43, 22.38, 23.40 and 23.80 expressed by 2θ degree using Cu-Kα radiation, with a 2θ angle measurement error being ±0.2.

Preferably, the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has an X-ray powder diffraction pattern having a diffraction angle (2θ) and interplanar spacing (d value) as shown in Table 2, with the 2θ angle measurement error being ±0.2.

TABLE 2

Diffraction angle and interplanar spacing results of X-ray powder diffraction pattern of crystalline form

| 2θ (±0.2°) | d (Å) |
|---|---|
| 5.52 | 16.01 |
| 11.10 | 7.96 |
| 12.30 | 7.19 |
| 16.73 | 5.30 |
| 18.86 | 4.70 |
| 19.43 | 4.56 |
| 22.38 | 3.97 |
| 23.40 | 3.80 |
| 23.80 | 3.74 |

Preferably, the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has an X-ray powder diffraction pattern substantially as shown in FIG. 3.

Preferably, the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has a DSC-TGA pattern substantially as shown in FIG. 4.

The present invention also provides a method for preparing the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), comprising the steps of:

dissolving the compound of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) in an organic solvent, heating to obtain a clear solution, precipitating a crystal by stirring and cooling, collecting the crystal by filtration, and drying to obtain the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), wherein the organic solvent is one or more selected from the group consisting of methanol, ethanol, ethyl acetate, acetonitrile and methyl tert-butyl ether.

Preferably, in the method of the present invention for preparing the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), the step of heating comprises heating to a reflux temperature; and/or the step of precipitating a crystal by cooling comprises cooling to a temperature of 10-30° C.

The present invention also provides use of the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) in the manufacture of a medicament for preventing and/or treating cardiovascular and cerebrovascular diseases caused by platelet aggregation, and the cardiovascular and cerebrovascular diseases are, for example, coronary artery syndrome, myocardial infarction, myocardial ischemia, and the like.

The present invention also provides a method for preventing and/or treating cardiovascular and cerebrovascular diseases caused by platelet aggregation, the method comprises administering to a subject in need thereof a therapeutically effective amount of the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), and the cardiovascular and cerebrovascular diseases are, for example, coronary artery syndrome, myocardial infarction, myocardial ischemia, and the like.

The present invention also provides a pharmaceutical composition comprising the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) and a pharmaceutically acceptable carrier or excipient.

In certain embodiments of the present invention, the pharmaceutical composition is a solid oral preparation, a liquid oral preparation, or an injection; preferably, the solid oral preparation is a tablet, a capsule or a granule; the liquid oral preparation is a syrup or an oral solution; and/or the injection is a liquid injection, a powder for injection or a small-volume infusion solution.

In yet another aspect, the present invention also provides a crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), a preparation method and use thereof, as well as a pharmaceutical composition comprising the crystalline form B.

The crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has an X-ray powder diffraction pattern having diffraction peaks at 4.31, 8.66, 13.01, 17.42 and 19.52 expressed by 2θ degree using Cu-Ka radiation, with a 2θ angle measurement error being ±0.2.

Preferably, the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has an X-ray powder diffraction pattern having diffraction peaks at 4.31, 8.66, 10.29, 10.94, 13.01, 17.42, 19.52, 23.17, 24.22 and 24.92 expressed by 2θ degree using Cu-Ka radiation, with a 2θ angle measurement error being ±0.2.

Preferably, the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has an X-ray powder diffraction pattern having a diffraction angle (2θ) and interplanar spacing (d value) as shown in Table 3, with the 2θ angle measurement error being ±0.2.

TABLE 3

Diffraction angle and interplanar spacing results of
X-ray powder diffraction pattern of crystalline form

| 2θ (±0.2°) | d (Å) |
|---|---|
| 4.31 | 20.50 |
| 8.66 | 10.20 |
| 10.29 | 8.59 |
| 10.94 | 8.08 |
| 13.01 | 6.80 |
| 17.42 | 5.09 |
| 19.52 | 4.54 |
| 23.17 | 3.84 |
| 24.22 | 3.67 |
| 24.92 | 3.57 |

Preferably, the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has an X-ray powder diffraction pattern substantially as shown in FIG. 5.

Preferably, the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) has a DSC-TGA pattern substantially as shown in FIG. 6.

The present invention also provides a method for preparing the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), comprising the steps of: dissolving the compound of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) in acetic acid, heating to obtain a clear solution, precipitating a crystal by cooling, collecting the crystal by filtration, and drying to obtain the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2).

Preferably, in the method of the present invention for preparing the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), the step of heating comprises heating to a temperature of 60° C. to a reflux temperature; and/or the step of precipitating a crystal by cooling comprises cooling to a temperature of 20-30° C.

The present invention also provides use of the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) in the manufacture of a medicament for preventing and/or treating cardiovascular and cerebrovascular diseases caused by platelet aggregation, and the cardiovascular and cerebrovascular diseases are, for example, coronary artery syndrome, myocardial infarction, myocardial ischemia, and the like.

The present invention also provides a method for preventing and/or treating cardiovascular and cerebrovascular diseases caused by platelet aggregation, the method comprises administering to a subject in need thereof a therapeutically effective amount of the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), and the cardiovascular and cerebrovascular diseases are, for example, coronary artery syndrome, myocardial infarction, myocardial ischemia, and the like.

The present invention also provides a pharmaceutical composition comprising the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) and a pharmaceutically acceptable carrier or excipient.

In certain embodiments of the present invention, the pharmaceutical composition is a solid oral preparation, a liquid oral preparation, or an injection; preferably, the solid oral preparation is a tablet, a capsule or a granule; the liquid oral preparation is a syrup or an oral solution; and/or the injection is a liquid injection, a powder for injection or a small-volume infusion solution.

In another aspect, the present invention also provides a crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3), a preparation method and use thereof, as well as a pharmaceutical composition comprising the crystalline form A.

The crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3) has an X-ray powder diffraction pattern having diffraction peaks at 5.71, 11.49, 17.28, 19.57 and 23.14 expressed by 2θ degree using Cu-Ka radiation, with a 2θ angle measurement error being ±0.2.

Preferably, the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3) has an X-ray powder diffraction pattern having diffraction peaks at 5.71, 11.49, 12.43, 15.95, 16.56, 17.28, 19.57, 23.14, 23.66, 24.98 and 26.09 expressed by 2θ degree using Cu-Ka radiation, with a 2θ angle measurement error being ±0.2.

Preferably, the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3) has an X-ray powder diffraction pattern having a diffraction angle (2θ) and interplanar spacing (d value) as shown in Table 4, with the 2θ angle measurement error being ±0.2.

TABLE 4

Diffraction angle and interplanar spacing results of
X-ray powder diffraction pattern of crystalline form

| 2θ (±0.2°) | d (Å) |
|---|---|
| 5.71 | 15.46 |
| 11.49 | 7.70 |
| 12.43 | 7.12 |
| 15.95 | 5.55 |

TABLE 4-continued

Diffraction angle and interplanar spacing results of
X-ray powder diffraction pattern of crystalline form

| 2θ (±0.2°) | d (Å) |
|---|---|
| 16.56 | 5.35 |
| 17.28 | 5.13 |
| 19.57 | 4.53 |
| 23.14 | 3.84 |
| 23.66 | 3.76 |
| 24.98 | 3.56 |
| 26.09 | 3.41 |

Preferably, the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3) has an X-ray powder diffraction pattern substantially as shown in FIG. 7.

Preferably, the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3) has a DSC-TGA pattern substantially as shown in FIG. 8.

The present invention also provides a method for preparing the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3), comprising the steps of: dissolving the compound of methyl (S,E)-2-(2-chlorophenyl)-2-(2-(2,4-pentadienoyloxy)-6,7-dihydrothieno[3,2-c]pyridin-5(4H)-yl)-acetate (I-3) in methanol, heating to obtain a clear solution, precipitating a crystal by stirring and cooling, collecting the crystal by filtration, and drying to obtain the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3).

Preferably, in the method of the present invention for preparing the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3), the step of heating comprises heating to a reflux temperature; and/or the step of precipitating a crystal by cooling comprises cooling to a temperature of 10-30° C.

The present invention also provides use of the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3) in the manufacture of a medicament for preventing and/or treating cardiovascular and cerebrovascular diseases caused by platelet aggregation, and the cardiovascular and cerebrovascular diseases are, for example, coronary artery syndrome, myocardial infarction, myocardial ischemia, and the like.

The present invention also provides a method for preventing and/or treating cardiovascular and cerebrovascular diseases caused by platelet aggregation, the method comprises administering to a subject in need thereof a therapeutically effective amount of the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3), and the cardiovascular and cerebrovascular diseases are, for example, coronary artery syndrome, myocardial infarction, myocardial ischemia, and the like.

The present invention also provides a pharmaceutical composition comprising the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3) and a pharmaceutically acceptable carrier or excipient.

In certain embodiments of the present invention, the pharmaceutical composition is a solid oral preparation, a liquid oral preparation, or an injection; preferably, the solid oral preparation is a tablet, a capsule or a granule; the liquid oral preparation is a syrup or an oral solution; and/or the injection is a liquid injection, a powder for injection or a small-volume infusion solution.

In yet another aspect, the present invention also provides a crystalline form A of methyl (S,E)-2-(2-chlorophenyl)-2-(2-(2-pentenoyloxy)-6,7-dihydrothieno[3,2-c]pyridin-5(4H)-yl)-acetate (I-4), a preparation method and use thereof, as well as a pharmaceutical composition comprising the crystalline form A.

The crystalline form A of methyl (S,E)-2-(2-chlorophenyl)-2-(2-(2-pentenoyloxy)-6,7-dihydrothieno[3,2-c]pyridin-5(4H)-yl)-acetate (I-4) has an X-ray powder diffraction pattern having diffraction peaks at 5.32, 16.09, 18.28, 20.68 and 21.51 expressed by 2θ degree using Cu-Ka radiation, with a 2θ angle measurement error being ±0.2.

Preferably, the crystalline form A of methyl (S,E)-2-(2-chlorophenyl)-2-(2-(2-pentenoyloxy)-6,7-dihydrothieno[3,2-c]pyridin-5(4H)-yl)-acetate (I-4) has an X-ray powder diffraction pattern having diffraction peaks at 5.32, 10.68, 12.98, 14.57, 16.09, 17.64, 18.28, 19.83, 20.68 and 21.51 expressed by 2θ degree using Cu-Ka radiation, with a 2θ angle measurement error being ±0.2.

Preferably, the crystalline form A of methyl (S,E)-2-(2-chlorophenyl)-2-(2-(2-pentenoyloxy)-6,7-dihydrothieno[3,2-c]pyridin-5(4H)-yl)-acetate (I-4) has an X-ray powder diffraction pattern having a diffraction angle (2θ) and interplanar spacing (d value) as shown in Table 5, with the 2θ angle measurement error being ±0.2.

TABLE 5

Diffraction angle and interplanar spacing results of
X-ray powder diffraction pattern of crystalline form

| 2θ (±0.2°) | d (Å) |
|---|---|
| 5.32 | 16.60 |
| 10.68 | 8.28 |
| 12.98 | 6.81 |
| 14.57 | 6.07 |
| 16.09 | 5.50 |
| 17.64 | 5.02 |
| 18.28 | 4.85 |
| 19.83 | 4.47 |
| 20.68 | 4.29 |
| 21.51 | 4.13 |

Preferably, the crystalline form A of methyl (S,E)-2-(2-chlorophenyl)-2-(2-(2-pentenoyloxy)-6,7-dihydrothieno[3,2-c]pyridin-5(4H)-yl)-acetate (I-4) has an X-ray powder diffraction pattern substantially as shown in FIG. 9.

Preferably, the crystalline form A of methyl (S,E)-2-(2-chlorophenyl)-2-(2-(2-pentenoyloxy)-6,7-dihydrothieno[3,2-c]pyridin-5(4H)-yl)-acetate (I-4) has a DSC-TGA pattern substantially as shown in FIG. 10.

The present invention also provides a method for preparing the crystalline form A of methyl (S,E)-2-(2-chlorophenyl)-2-(2-(2-pentenoyloxy)-6,7-dihydrothieno[3,2-c]pyridin-5(4H)-yl)-acetate (I-4), comprising the steps of:

dissolving the compound of methyl (S,E)-2-(2-chlorophenyl)-2-(2-(2-pentenoyloxy)-6,7-dihydrothieno[3,2-c]pyridin-5(4H)-yl)-acetate (I-4) in an organic solvent, heating to obtain a clear solution, precipitating a crystal by stirring and cooling, collecting the crystal by filtration, and drying to obtain the crystalline form A of methyl (S,E)-2-(2-chlorophenyl)-2-(2-(2-pentenoyloxy)-6,7-dihydrothieno[3,2-c]pyridin-5(4H)-yl)-acetate (I-4), wherein the organic solvent is one or more selected from the group consisting of methanol, ethanol, toluene, ethyl acetate, acetone, acetonitrile and methyl tert-butyl ether.

Preferably, in the method of the present invention for preparing the crystalline form A of methyl (S,E)-2-(2-chlorophenyl)-2-(2-(2-pentenoyloxy)-6,7-dihydrothieno[3,2-c] pyridin-5(4H)-yl)-acetate (I-4), the step of heating comprises heating to a reflux temperature; and/or the step of precipitating a crystal by cooling comprises cooling to a temperature of 10-30° C.

The present invention also provides use of the crystalline form A of methyl (S,E)-2-(2-chlorophenyl)-2-(2-(2-pentenoyloxy)-6,7-dihydrothieno[3,2-c]pyridin-(4H)-yl)-acetate (I-4) in the manufacture of a medicament for preventing and/or treating cardiovascular and cerebrovascular diseases caused by platelet aggregation, and the cardiovascular and cerebrovascular diseases are, for example, coronary artery syndrome, myocardial infarction, myocardial ischemia, and the like.

The present invention also provides a method for preventing and/or treating cardiovascular and cerebrovascular diseases caused by platelet aggregation, the method comprises administering to a subject in need thereof a therapeutically effective amount of the crystalline form A of methyl (S,E)-2-(2-chlorophenyl)-2-(2-(2-pentenoyloxy)-6,7-dihydrothieno[3,2-c]pyridin-5(4H)-yl)-acetate (I-4), and the cardiovascular and cerebrovascular diseases are, for example, coronary artery syndrome, myocardial infarction, myocardial ischemia, and the like.

The present invention also provides a pharmaceutical composition comprising the crystalline form A of methyl (S,E)-2-(2-chlorophenyl)-2-(2-(2-pentenoyloxy)-6,7-dihydrothieno[3,2-c]pyridin-5(4H)-yl)-acetate (I-4) and a pharmaceutically acceptable carrier or excipient.

In certain embodiments of the present invention, the pharmaceutical composition is a solid oral preparation, a liquid oral preparation, or an injection; preferably, the solid oral preparation is a tablet, a capsule or a granule; the liquid oral preparation is a syrup or an oral solution; and/or the injection is a liquid injection, a powder for injection or a small-volume infusion solution.

In another aspect, the present invention also provides a crystalline form A of methyl (S,E)-2-(2-chlorophenyl)-2-(2-(2-hexenoyloxy)-6,7-dihydrothieno[3,2-c]pyridin-5(4H)-yl)-acetate (I-5), a preparation method and use thereof, as well as a pharmaceutical composition comprising the crystalline form A.

The crystalline form A of methyl (S,E)-2-(2-chlorophenyl)-2-(2-(2-hexenoyloxy)-6,7-dihydrothieno[3,2-c]pyridin-5(4H)-yl)-acetate (I-5) has an X-ray powder diffraction pattern having diffraction peaks at 5.58, 16.84, 19.46, 22.50 and 23.47 expressed by 2θ degree using Cu-Kα radiation, with a 2θ angle measurement error being ±0.2.

Preferably, the crystalline form A of methyl (S,E)-2-(2-chlorophenyl)-2-(2-(2-hexenoyloxy)-6,7-dihydrothieno[3, 2-c]pyridin-5(4H)-yl)-acetate (I-5) has an X-ray powder diffraction pattern having diffraction peaks at 5.58, 11.19, 12.21, 15.64, 16.84, 19.00, 19.46, 20.09, 22.50, 23.47, 23.99 and 25.81 expressed by 2θ degree using Cu-Kα radiation, with a 2θ angle measurement error being ±0.2.

Preferably, the crystalline form A of methyl (S,E)-2-(2-chlorophenyl)-2-(2-(2-hexenoyloxy)-6,7-dihydrothieno[3, 2-c]pyridin-5(4H)-yl)-acetate (I-5) has an X-ray powder diffraction pattern having a diffraction angle (2θ) and interplanar spacing (d value) as shown in Table 6, with the 2θ angle measurement error being ±0.2.

TABLE 6

Diffraction angle and interplanar spacing results of X-ray powder diffraction pattern of crystalline form

| 2θ (±0.2°) | d (Å) |
|---|---|
| 5.58 | 15.83 |
| 11.19 | 7.90 |
| 12.21 | 7.24 |
| 15.64 | 5.66 |
| 16.84 | 5.26 |
| 19.00 | 4.67 |
| 19.46 | 4.56 |
| 20.09 | 4.42 |
| 22.50 | 3.95 |
| 23.47 | 3.79 |
| 23.99 | 3.71 |
| 25.81 | 3.45 |

Preferably, the crystalline form A of methyl (S,E)-2-(2-chlorophenyl)-2-(2-(2-hexenoyloxy)-6,7-dihydrothieno[3, 2-c]pyridin-5(4H)-yl)-acetate (I-5) has an X-ray powder diffraction pattern substantially as shown in FIG. 11.

Preferably, the crystalline form A of methyl (S,E)-2-(2-chlorophenyl)-2-(2-(2-hexenoyloxy)-6,7-dihydrothieno[3, 2-c]pyridin-5(4H)-yl)-acetate (I-5) has a DSC-TGA pattern substantially as shown in FIG. 12.

The present invention also provides a method for preparing the crystalline form A of methyl (S,E)-2-(2-chlorophenyl)-2-(2-(2-hexenoyloxy)-6,7-dihydrothieno[3,2-c]pyridin-5(4H)-yl)-acetate (I-5), comprising the steps of: dissolving the compound of methyl (S,E)-2-(2-chlorophenyl)-2-(2-(2-hexenoyloxy)-6,7-dihydrothieno[3,2-c]pyridin-5(4H)-yl)-acetate (I-5) in an organic solvent, heating to obtain a clear solution, precipitating a crystal by stirring and cooling, collecting the crystal by filtration, and drying to obtain the crystalline form A of methyl (S,E)-2-(2-chlorophenyl)-2-(2-(2-hexenoyloxy)-6,7-dihydrothieno[3,2-c] pyridin-5(4H)-yl)-acetate (I-5), wherein the organic solvent is one or more selected from the group consisting of methanol, ethanol, acetone, acetonitrile and methyl tert-butyl ether.

Preferably, in the method of the present invention for preparing the crystalline form A of methyl (S,E)-2-(2-chlorophenyl)-2-(2-(2-hexenoyloxy)-6,7-dihydrothieno[3,2-c] pyridin-5(4H)-yl)-acetate (I-5), the step of heating comprises heating to a reflux temperature; and/or the step of precipitating a crystal by cooling comprises cooling to a temperature of 10-30° C.

The present invention also provides use of the crystalline form A of methyl (S,E)-2-(2-chlorophenyl)-2-(2-(2-hexenoyloxy)-6,7-dihydrothieno[3,2-c]pyridin-(4H)-yl)-acetate (I-5) in the manufacture of a medicament for preventing and/or treating cardiovascular and cerebrovascular diseases caused by platelet aggregation, and the cardiovascular and cerebrovascular diseases are, for example, coronary artery syndrome, myocardial infarction, myocardial ischemia, and the like.

The present invention also provides a method for preventing and/or treating cardiovascular and cerebrovascular diseases caused by platelet aggregation, the method comprises administering to a subject in need thereof a therapeutically effective amount of the crystalline form A of methyl (S,E)-2-(2-chlorophenyl)-2-(2-(2-hexenoyloxy)-6,7-dihydrothieno[3,2-c]pyridin-5(4H)-yl)-acetate (I-5), and the cardiovascular and cerebrovascular diseases are, for example, coronary artery syndrome, myocardial infarction, myocardial ischemia, and the like.

The present invention also provides a pharmaceutical composition comprising the crystalline form A of methyl (S,E)-2-(2-chlorophenyl)-2-(2-(2-hexenoyloxy)-6,7-dihydrothieno[3,2-c]pyridin-5(4H)-yl)-acetate (I-5) and a pharmaceutically acceptable carrier or excipient.

In certain embodiments of the present invention, the pharmaceutical composition is a solid oral preparation, a liquid oral preparation, or an injection; preferably, the solid oral preparation is a tablet, a capsule or a granule; the liquid oral preparation is a syrup or an oral solution; and/or the injection is a liquid injection, a powder for injection or a small-volume infusion solution.

The compound having the structure of formula (I) and the crystalline form of each compound of the present invention are effective in a relatively wide dosage range. For example, the daily dosage is in the range of 1 to 1000 mg/person, and it can be administered in one or several times. The actual dosage should be determined by a physician based on relevant conditions, including the physical condition of the subject being treated, the route of administration, age and weight of the patient, individual response to the drug, and the severity of the symptoms, and the like.

The inventors of the present application have surprisingly found that, the pharmacodynamic studies show that the compounds having the structures of formula (I) provided by the present invention have a significant inhibitory effect on platelet aggregation, and the therapeutic effect is better than clopidogrel; the pharmacokinetic studies show that the compounds having the structures of formula (I) of the present invention can be rapidly and effectively converted into pharmacologically active metabolites to exert their inhibitory effect on platelet aggregation, and will not cause resistance resulted from gene polymorphism of related enzymes of population; the safety evaluation shows that the compounds of the formula (I) of the present invention have high safety; the pharmaceutical research shows that the compounds having the structures of formula (I) of the present invention are easy to be prepared and exist in a solid form; and the stability study shows that the compounds having the structures of formula (I) of the present invention have good stability, which facilitates the formulation, storage and use of agents.

At the same time, the inventors of the present application also surprisingly found that the compounds having the structures of formula (I) of the present invention exist in a solid form, while compounds having structures similar to the compounds having the structures of formula (I) of the present invention, which only have minor changes in the unsaturated aliphatic olefinic bond, such as Example compounds D-1, D-2, D-3, D-4, D-5, D-6 and D-7, are oils and are difficult to form salts, which are extremely adverse to drugability.

The results of various studies show that the compounds having the structures of formula (I) of the present invention obviously have unexpected effects compared with those disclosed in the prior arts. The compounds having the structures of formula (I) of the present invention exist in a solid form, which not only can solve the problem of clopidogrel resistance, but also can solve the problem of severe hemorrhagic side effect and poor safety of some drugs, as well as the problem of poor stability of existing compounds. It can be developed into an ADP receptor antagonist antiplatelet agent with clear therapeutic effects, no resistance and better stability.

Each crystalline form of the compounds having the structures of formula (I) of the present invention also have the above-mentioned effects in pharmacodynamics, pharmacokinetics, safety and stability.

BRIEF DESCRIPTION OF THE DRAWINGS

Hereinafter, embodiments of the present invention will be described in detail with reference to the drawings, in which.

BEST MODE FOR CARRYING OUT THE INVENTION

Figure 1:
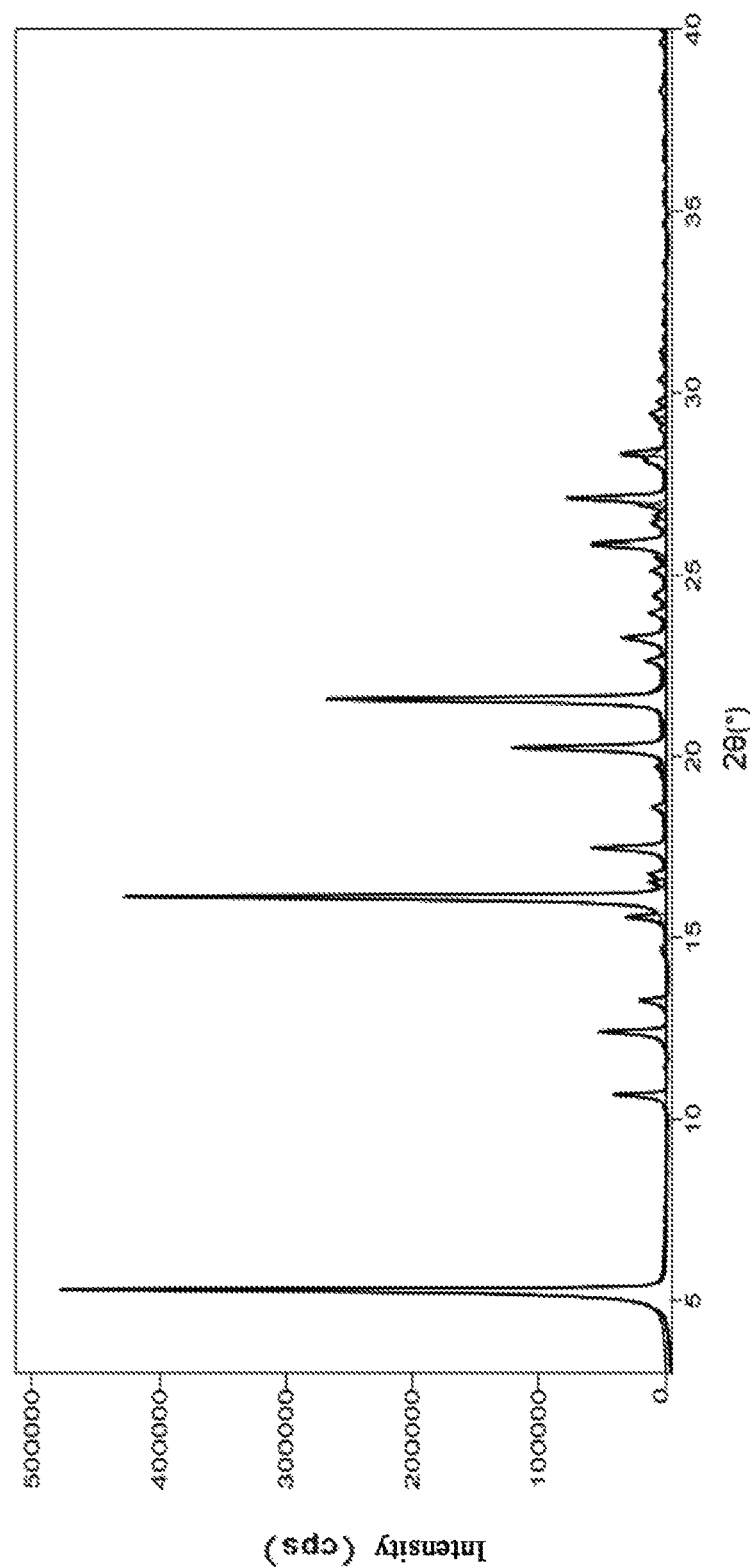
FIG. 1 shows the X-ray powder diffraction pattern of crystalline form A of the compound of methyl (S,E)-2-(2-chlorophenyl)-2-(2-(2-butenoyloxy)-6,7-dihydrothieno[3,2-c]pyridin-5(4H)-yl)-acetate (I-1) of the present invention.

The present invention is further described with reference to the examples. The examples are only for explanation and illustration, and are not meant to limit the scope of the present invention in any way.

Example 1

Methyl (S,E)-2-(2-chlorophenyl)-2-(2-(2-butenoyloxy)-6,7-dihydrothieno[3,2-c]pyridin-5(4H)-yl)-acetate (I-1)

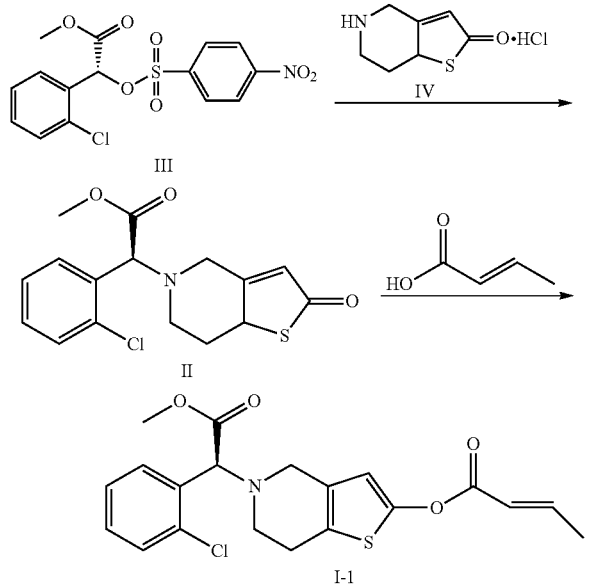

To a reaction flask were added methyl (R)-2-(2-chlorophenyl)-2-(4-nitrobenzenesulfonyloxy)acetate (Compound II) (40.00 g), 5,6,7,7a-tetrahydro-thieno[3,2-c]pyridin-2(4H)-one hydrochloride (Compound IV) (24.00 g), potassium carbonate (60.00 g), and acetonitrile (500 mL). The reaction mixture was stirred at 25-35° C. for 12 h, filtered, and the filtrate was concentrated under reduced pressure to remove the solvent, and then ethanol (150 mL) was added. The mixture was stirred and dispersed for 30 min, filtered and dried to obtain methyl (2S)-2-(2-chlorophenyl)-2-(2-oxo-7,7a-dihydrothieno[3,2-c]pyridin-5(2H, 4H,6H)-yl)acetate (compound II) (25.40 g).

To a reaction flask were added trans-2-butenoic acid (7.80 g), Compound II (20.00 g), DMAP (2.00 g), and dichloromethane (200 mL), and triethylamine (12.5 mL) and EDCI (18.00 g) were added under stirring. The reaction mixture was stirred at 20-25° C. for 2-3 h. The reaction solution was washed with water (100 mL×1), 5% aqueous hydrochloric acid solution (100 mL×1), and water (100 mL×2), dried over anhydrous sodium sulfate and filtered. The solvent was evaporated under reduced pressure, methanol (100 mL) was added. The mixture was stirred and dispersed, filtered to obtain an off-white solid (11.00 g).

$^1$H-NMR (DMSO-d$_6$), δ(ppm): 1.92-1.94 (m, 3H), 2.68-2.87 (m, 4H), 3.53 (s, 2H), 3.65 (s, 3H), 4.84 (s, 1H), 6.08-6.12 (m, 1H), 6.46 (s, 1H), 7.09-7.18 (m, 1H), 7.34-7.41 (m, 2H), 7.46-7.50 (m, 1H), 7.56-7.59 (m, 1H); [M+H]$^+$: 406.0863.

Example 2

Methyl (S)-2-(2-chlorophenyl)-2-(2-((2E,4E)-2,4-hexadienoyloxy)-6,7-dihydrothieno[3,2-c]pyridin-5(4H)-yl)-acetate (I-2)

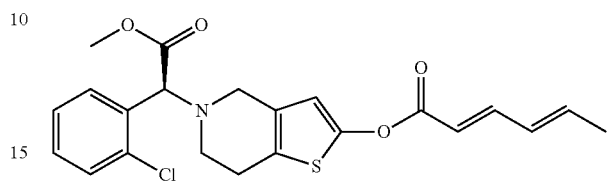

To a reaction flask were added sorbic acid (12.80 g), Compound II (20.00 g), DMAP (1.00 g), and dichloromethane (300 mL), and triethylamine (15.0 mL) and EDCI (24.00 g) were added under stirring. The reaction mixture was stirred at room temperature for 2-3 h, to which 5% aqueous hydrochloric acid solution (600 mL) was added. After stirring for 5 minutes, the phases were allowed to separate. The organic phase was washed with saturated sodium bicarbonate solution (400 mL), dried over anhydrous sodium sulfate and filtered. The filtrate was evaporated to dryness and separated by silica gel column chromatography ($V_{ethyl\ acetate}:V_{petroleum\ ether}=1:7$) to obtain a pale yellow solid (12.00 g).

$^1$H-NMR (DMSO-d$_6$), δ(ppm): 1.84 (d, 3H), 2.68-2.87 (m, 4H), 3.53 (s, 2H), 3.65 (s, 3H), 4.84 (s, 1H), 6.02-6.06 (d, 1H), 6.35-6.42 (m, 2H), 6.46 (s, 1H), 7.34-7.50 (m, 4H), 7.56-7.59 (m, 1H); [M+H]$^+$: 432.1024.

Example 3

Methyl (S,E)-2-(2-chlorophenyl)-2-(2-(2,4-pentadienoyloxy)-6,7-dihydrothieno[3,2-c]pyridin-5(4H)-yl)-acetate (I-3)

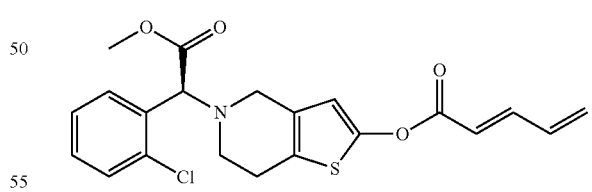

Compound I-3 was obtained in the same manner as in Example 2 except that (E)-2,4-pentadienoic acid was used instead of sorbic acid, and N,N-diisopropylethylamine was used instead of triethylamine. Compound I-3 was a pale yellow solid.

$^1$H-NMR (DMSO-d$_6$), δ(ppm): 2.66-2.85 (m, 4H), 3.56 (s, 2H), 3.63 (s, 3H), 4.82 (s, 1H), 5.63 (d, 1H), 5.83 (d, 1H), 6.20 (d, 1H), 6.46 (s, 1H), 6.55-6.65 (m, 1H), 7.31-7.47 (m, 4H), 7.55-7.57 (m, 1H); [M+H]$^+$: 418.0865.

Example 4

Methyl (S,E)-2-(2-chlorophenyl)-2-(2-(2-pentenoyloxy)-6,7-dihydrothieno[3,2-c]pyridin-5(4H)-yl)-acetate (I-4)

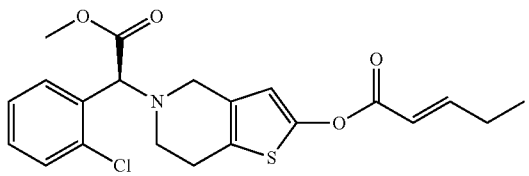 [SMILES: CC/C=C/C(=O)Oc1cc2c(s1)CCN([C@H](C(=O)OC)c1ccccc1Cl)C2]

Compound I-4 was obtained in the same manner as in Example 2 except that trans-2-pentenoic acid was used instead of sorbic acid. Compound I-4 was an off-white solid.

$^1$H-NMR (DMSO-d$_6$), δ(ppm): 1.03 (t, 3H), 2.24-2.29 (m, 2H), 2.68-2.87 (m, 4H), 3.54 (s, 2H), 3.65 (s, 3H), 4.84 (s, 1H), 6.03 (d, 1H), 6.46 (s, 1H), 7.15-7.22 (m, 1H), 7.34-7.40 (m, 2H), 7.47-7.49 (m, 1H), 7.58-7.59 (m, 1H); [M+H]$^+$: 420.1027.

Example 5

Methyl (S,E)-2-(2-chlorophenyl)-2-(2-(2-hexenoyloxy)-6,7-dihydrothieno[3,2-c]pyridin-5(4H)-yl)-acetate (I-5)

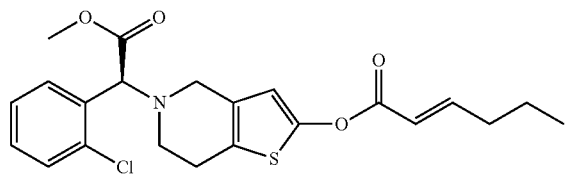 [SMILES: CCC/C=C/C(=O)Oc1cc2c(s1)CCN([C@H](C(=O)OC)c1ccccc1Cl)C2]

Compound I-5 was obtained in the same manner as in Example 2 except that trans-2-hexenoic acid was used instead of sorbic acid. Compound I-5 was an off-white solid.

$^1$H-NMR (DMSO-d$_6$), δ(ppm): 0.89 (t, 3H), 1.43-1.50 (m, 2H), 2.22-2.27 (m, 2H), 2.68-2.86 (m, 4H), 3.53 (s, 2H), 3.65 (s, 3H), 4.84 (s, 1H), 6.07 (d, 1H), 6.47 (s, 1H), 7.09-7.16 (m, 1H), 7.34-7.41 (m, 2H), 7.48-7.50 (m, 1H), 7.56-7.59 (m, 1H); [M+H]$^+$: 434.1182.

Example 6

Methyl (S)-2-(2-chlorophenyl)-2-(2-acryloyloxy-6,7-dihydrothieno[3,2-c]pyridin-5(4H)-yl)-acetate (D-1)

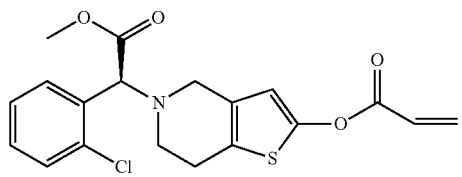 [SMILES: C=CC(=O)Oc1cc2c(s1)CCN([C@H](C(=O)OC)c1ccccc1Cl)C2]

Compound D-1 was obtained in the same manner as in Example 2 except that acrylic acid was used instead of sorbic acid. Compound D-1 was an oil.

$^1$H-NMR (DMSO-d$_6$), δ(ppm): 2.69-2.85 (m, 4H), 3.54 (s, 2H), 3.65 (s, 3H), 4.85 (s, 1H), 6.17 (d, 1H), 6.34-6.40 (m, 1H), 6.51-6.56 (m, 2H), 7.36-7.41 (m, 2H), 7.48-7.50 (m, 1H), 7.57-7.59 (m, 1H); [M+H]$^+$: 392.0711.

Example 7

Methyl (S)-2-(2-chlorophenyl)-2-(2-(3-methyl-2-butenoyloxy)-6,7-dihydrothieno[3,2-c]pyridin-5(4H)-yl)-acetate (D-2)

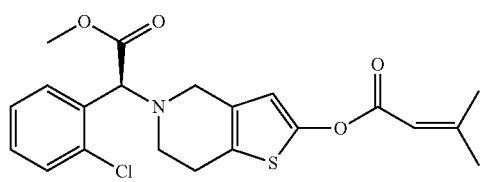 [SMILES: COC(=O)[C@H](c1ccccc1Cl)N1CCc2sc(OC(=O)C=C(C)C)cc2C1]

Compound D-2 was obtained in the same manner as in Example 2 except that 3-methyl-2-butenoic acid was used instead of sorbic acid. Compound D-2 was an oil.

$^1$H-NMR (DMSO-d$_6$), δ(ppm): 1.95 (s, 3H), 2.16 (s, 3H), 2.68-2.84 (m, 4H), 3.53 (s, 2H), 3.65 (s, 3H), 4.84 (s, 1H), 5.88 (s, 1H), 6.40 (s, 1H), 7.35-7.40 (m, 2H), 7.46-7.49 (m, 1H), 7.57-7.60 (m, 1H); [M+H]$^+$: 420.1024.

Example 8

Methyl(S,E)-2-(2-chlorophenyl)-2-(2-(2-heptenoyloxy)-6,7-dihydrothieno[3,2-c]pyridin-5(4H)-yl)-acetate (D-3)

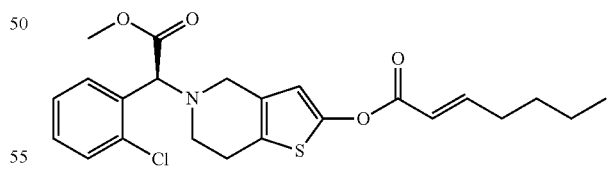

Compound D-3 was obtained in the same manner as in Example 2 except that trans-2-heptenoic acid was used instead of sorbic acid. Compound D-3 was an oil.

$^1$H-NMR (DMSO-d$_6$), δ(ppm): 0.80-0.89 (m, 3H), 1.22-1.35 (m, 2H), 1.38-1.46 (m, 2H), 2.23-2.28 (m, 2H), 2.68-2.85 (m, 4H), 3.53 (s, 2H), 3.65 (s, 3H), 4.84 (s, 1H), 6.05 (d, 1H), 6.46 (s, 1H), 7.09-7.16 (m, 1H), 7.34-7.40 (m, 2H), 7.48 (d, 1H), 7.57 (d, 1H); [M+H]$^+$: 448.1348.

Example 9

Methyl (S)-2-(2-chlorophenyl)-2-(2-(2-methylacryloyloxy)-6,7-dihydrothieno[3,2-c]pyridin-5(4H)-yl)-acetate (D-4)

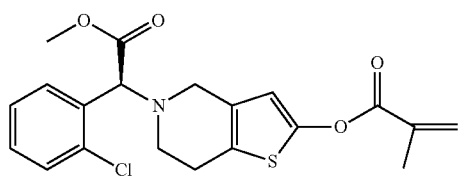 [SMILES: C=C(C)C(=O)Oc1cc2c(s1)CCN([C@H](C(=O)OC)c1ccccc1Cl)C2]

Compound D-4 was obtained in the same manner as in Example 2 except that 2-methacrylic acid was used instead of sorbic acid. Compound D-4 was an oil.
¹H-NMR (DMSO-d₆), δ(ppm): 1.96 (s, 3H), 2.69-2.86 (m, 4H), 3.54 (s, 2H), 3.65 (s, 3H), 4.85 (s, 1H), 5.91 (s, 1H), 6.25 (s, 1H), 6.50 (s, 1H), 7.34-7.41 (m, 2H), 7.48-7.50 (m, 1H), 7.57-7.59 (m, 1H); [M+H]⁺: 406.0866.

Example 10

Methyl (S,Z)-2-(2-chlorophenyl)-2-(2-(2-methyl-2-butenoyloxy)-6,7-dihydrothieno[3,2-c]pyridin-5(4H)-yl)acetate (D-5)

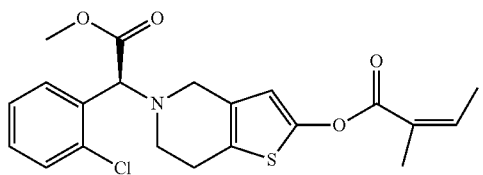 [SMILES: C/C=C(/C)C(=O)Oc1cc2c(s1)CCN([C@H](C(=O)OC)c1ccccc1Cl)C2]

Compound D-5 was obtained in the same manner as in Example 2 except that (Z)-2-methyl-2-butenoic acid was used instead of sorbic acid. Compound D-5 was an oil.
¹H-NMR (DMSO-d₆), (ppm): 1.94 (t, 3H), 1.99 (t, 3H), 2.69-2.86 (m, 4H), 3.54 (s, 2H), 3.65 (s, 3H), 4.84 (s, 1H), 6.36-6.38 (m, 1H), 6.49 (s, 1H), 7.35-7.41 (m, 2H), 7.48-7.50 (m, 1H), 7.57-7.59 (m, 1H); [M+H]⁺: 420.1007.

Example 11

Methyl (S,E)-2-(2-chlorophenyl)-2-(2-(2-methyl-2-butenoyloxy)-6,7-dihydrothieno[3,2-c]pyridin-5(4H)-yl)-acetate (D-6)

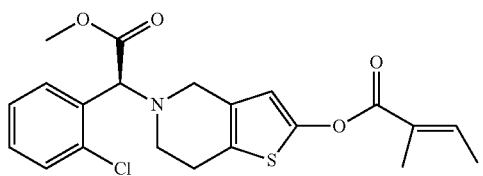 [SMILES: C/C=C(\C)C(=O)Oc1cc2c(s1)CCN([C@H](C(=O)OC)c1ccccc1Cl)C2]

Compound D-6 was obtained in the same manner as in Example 2 except that (E)-2-methyl-2-butenoic acid was used instead of sorbic acid. Compound D-6 was an oil.
¹H-NMR (DMSO-d₆), δ(ppm): 1.81-1.85 (m, 6H), 2.68-2.85 (m, 4H), 3.54 (s, 2H), 3.65 (s, 3H), 4.84 (s, 1H), 6.46 (s, 1H), 7.00-7.05 (m, 1H), 7.34-7.41 (m, 2H), 7.48-7.50 (m, 1H), 7.56-7.59 (m, 1H); [M+H]: 420.1008.

Example 12

Methyl (S)-2-(2-chlorophenyl)-2-(2-(2-phenylacryloyloxy)-6,7-dihydrothieno[3,2-c]pyridin-5(4H)-yl)-acetate (D-7)

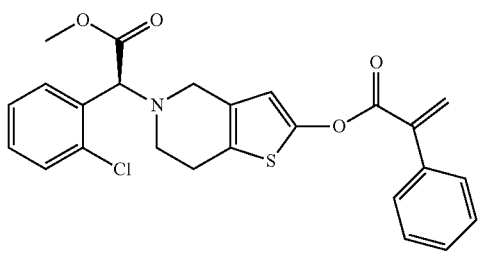 [SMILES: C=C(C(=O)Oc1cc2c(s1)CCN([C@H](C(=O)OC)c1ccccc1Cl)C2)c1ccccc1]

Compound D-7 was obtained in the same manner as in Example 2 except that 2-phenyl-2-butenoic acid was used instead of sorbic acid. Compound D-7 was an oil.
¹H-NMR (DMSO-d₆), (ppm): 2.70-2.84 (m, 4H), 3.55 (s, 2H), 3.65 (s, 3H), 4.85 (s, 1H), 6.25 (s, 1H), 6.52 (s, 1H), 6.54 (s, 1H), 7.36-7.42 (m, 5H), 7.46-7.50 (m, 3H), 7.57-7.59 (m, 1H); [M+H]⁺: 468.1008.

Example 13

Methyl (S,E)-2-(2-chlorophenyl)-2-(2-(3-(4-methoxyphenyl)acryloyloxy)-6,7-dihydrothieno[3,2-c]pyridin-5(4H)-yl)-acetate (D-8)

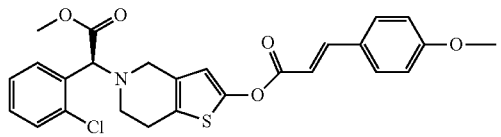 [SMILES: COC(=O)[C@H](c1ccccc1Cl)N1CCc2sc(OC(=O)/C=C/c3ccc(OC)cc3)cc2C1]

Compound D-8 was obtained in the same manner as in Example 2 except that p-methoxycinnamic acid was used instead of sorbic acid. Compound D-8 was a pale orange solid.
¹H-NMR (DMSO-d₆), δ(ppm): 2.69-2.86 (m, 4H), 3.51 (s, 2H), 3.66 (s, 3H), 3.80 (s, 3H), 4.85 (s, 1H), 6.49 (s, 1H), 6.67 (d, 1H), 6.99 (d, 2H), 7.34-7.41 (m, 2H), 7.49 (d, 1H), 7.59 (d, 1H), 7.75 (d, 2H), 7.82 (d, 1H); [M+H]⁺: 498.1132.

Example 14

Methyl (S,E)-2-(2-chlorophenyl)-2-(2-acetoxy-6,7-dihydrothieno[3,2-c]pyridin-5(4H)-yl)-acetate Hydrochloride (D-9, B is Methyl)

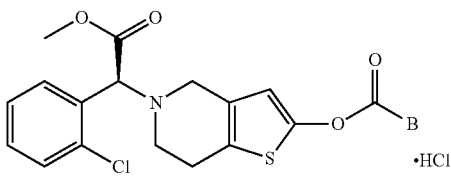

To a 500 mL three-necked flask were added compound H (20 g), dichloromethane (200 mL), triethylamine (16.4 mL) and acetic anhydride (7.8 mL) successively. The reaction mixture was stirred at room temperature for 5 h. The reaction solution was washed successively with distilled water (100 mL), 5% aqueous HCl solution (120 mL), saturated sodium bicarbonate aqueous solution (60 mL) and saturated brine (60 mL), dried over anhydrous sodium sulfate, filtered and separated by silica gel column chromatography ($V_{ethyl\ acetate}:V_{petroleum\ ether}=1:5$) to obtain a yellow oil (15.00 g, yield 66.42%), i.e. compound methyl (S,E)-2-(2-chlorophenyl)-2-(2-acetoxy-6,7-dihydrothieno[3,2-c]pyridin-5(4H)-yl)-acetate (B is methyl), which is an oil.

$^1$H-NMR (DMSO-$d_6$), δ(ppm): 2.25 (s, 3H), 2.67-2.85 (m, 4H), 3.52 (s, 3H), 3.65 (s, 3H), 4.84 (s, 1H), 6.42 (s, 1H), 7.33-7.41 (m, 2H), 7.47-7.50 (m, 1H), 7.56-7.59 (m, 1H); [M+H]$^+$: 380.0710.

To a 100 mL three-necked flask were added the obtained oil (3.00 g) and ethyl acetate (30 mL), and the reaction mixture was stirred to dissolve. 2.2 mol/L HCl-ethyl acetate solution (8.60 mL) was added dropwise at 0-5° C. under stirring and a solid was precipitated out. After the addition was completed, the mixture was raised to room temperature to react for 2 h, filtered, and the filter cake was washed with ethyl acetate (20 mL×3) to obtain a white solid.

To the reaction flask was added the obtained white solid, followed by ethyl acetate (40 mL) and absolute ethanol (10 mL). The mixture was heated to reflux under stirring to obtain a clear solution, and then cooled to room temperature for crystallization. The temperature was maintained, and stirring was continued for 2 h. The resulting mixture was filtered and dried under vacuum at 35-40° C. for 3-4 h to obtain compound methyl (S,E)-2-(2-chlorophenyl)-2-(2-acetoxy-6,7-dihydrothieno[3,2-c]pyridin-5(4H)-yl)-acetate hydrochloride (D-9, B is methyl) as a white solid (1.00 g).

In the the Examples of the Present Invention, the Measurement Conditions of the Crystalline Form are as Follows:

X-Ray Powder Diffraction Conditions:
Instrument: Rigaku SmartLab 3 kW powder X-ray diffractometer
Ray: Cu-Ka radiation, λ=1.5419 Å, 2θ=3°~40°
Voltage: 40 kV
Electric current: 40 mA
Scan speed: 10°/min
DS/SS=1/2°
RS: 20 mm DSC-TGA Conditions:
Instrument: METTLER TOLEDO TGA/DSC1 Simultaneous Thermal Analyzer
Heating rate: 10° C./min
Temperature range: 30° C.~170° C.
Reference compound: $Al_2O_3$ Example 15

Crystalline form A of methyl (S,E)-2-(2-chlorophenyl)-2-(2-(2-butenoyl-oxy)-6,7-dihydrothieno[3,2-c]pyridin-5(4H)-yl)-acetate (I-1)

To a reaction flask was added compound I-1 (5.00 g), and absolute ethanol (100 mL) was added. The reaction mixture was heated to reflux to obtain a clear solution, and then cooled to 15-25° C. under stirring and maintained for 2 h while stirring. The resulting mixture was filtered and dried under vacuum at 40-45° C. for 5 h to obtain a white solid (4.30 g, yield: 86.00%).

Figure 2:
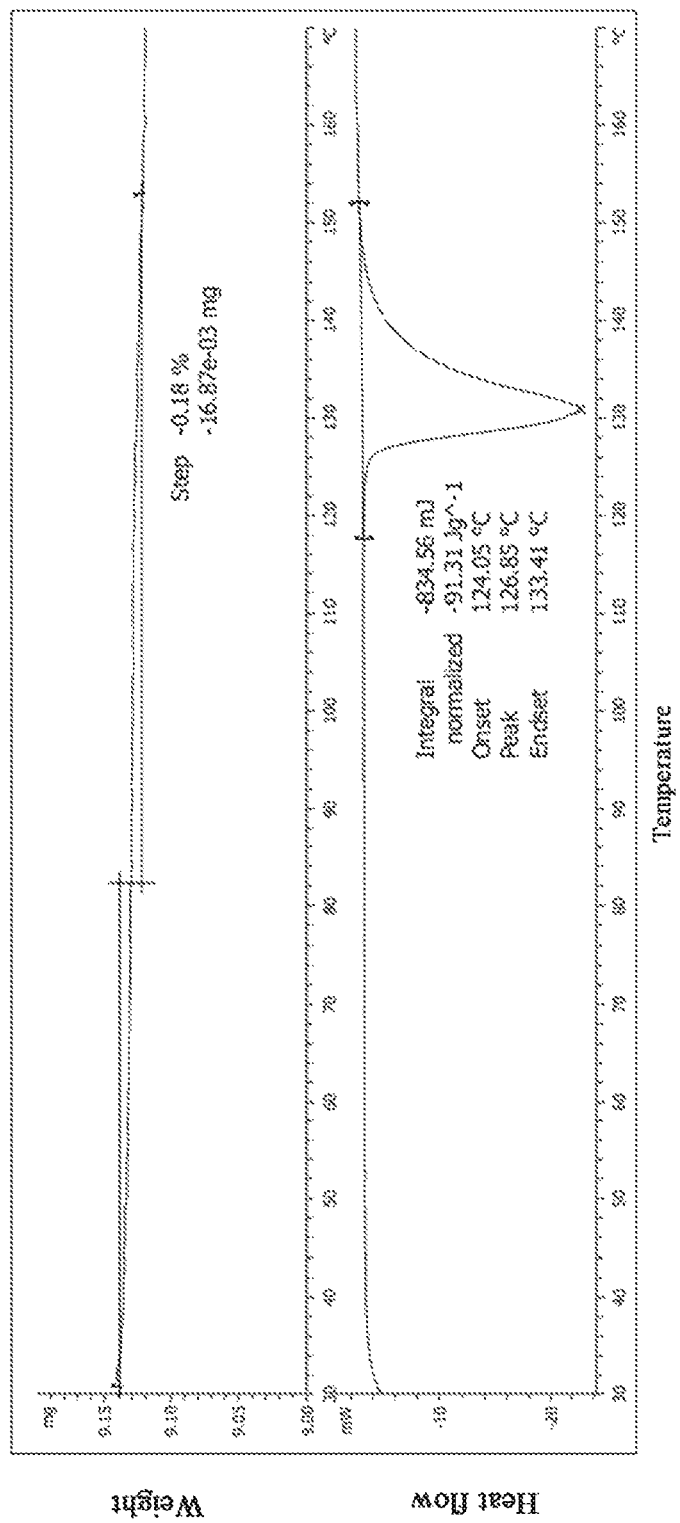
FIG. 2 shows the DSC-TGA (differential scanning calorimetry-thermogravimetric analysis) pattern of crystalline form A of the compound of methyl (S,E)-2-(2-chlorophenyl)-2-(2-(2-butenoyloxy)-6,7-dihydrothieno[3,2-c]pyridin-5(4H)-yl)-acetate (I-1) of the present invention.

The X-ray powder diffraction pattern and DSC-TGA patter of this product are shown in FIG. 1 and FIG. 2, respectively. The product is crystalline form A of methyl (S,E)-2-(2-chlorophenyl)-2-(2-(2-butenoyloxy)-6,7-dihydrothieno[3,2-c]pyridin-5(4H)-yl)-acetate (I-1).

Example 16

Crystalline form A of methyl (S,E)-2-(2-chlorophenyl)-2-(2-(2-butenoyl-oxy)-6,7-dihydrothieno[3,2-c]pyridin-5(4H)-yl)-acetate (I-1)

To a reaction flask was added compound I-1 (2.00 g), and methanol (60 mL) was added. The reaction mixture was heated to reflux to obtain a clear solution, and then cooled to 20-25° C. under stirring and maintained for 2 h while stirring. The resulting mixture was filtered and dried under vacuum at 40-45° C. for 5 h to obtain a white solid (1.60 g, yield: 80.00%).

The resulting white solid was determined by X-ray powder diffraction and DSC-TGA as crystalline form A of methyl (S,E)-2-(2-chlorophenyl)-2-(2-(2-butenoyloxy)-6,7-dihydrothieno[3,2-c]pyridin-5(4H)-yl)-acetate (I-1).

Example 17

Crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2)

To a reaction flask was added compound I-2 (3.00 g), and absolute ethanol (10 mL) was added. The reaction mixture was heated to reflux to obtain a clear solution. The resulting solution was allowed to cool down to 20-25° C. and the temperature was maintained for 2 h for crystallization. The resulting mixture was filtered and dried under vacuum at 40-45° C. for 10 h to obtain a pale yellow solid (2.20 g, yield: 73.33%).

Figure 3:
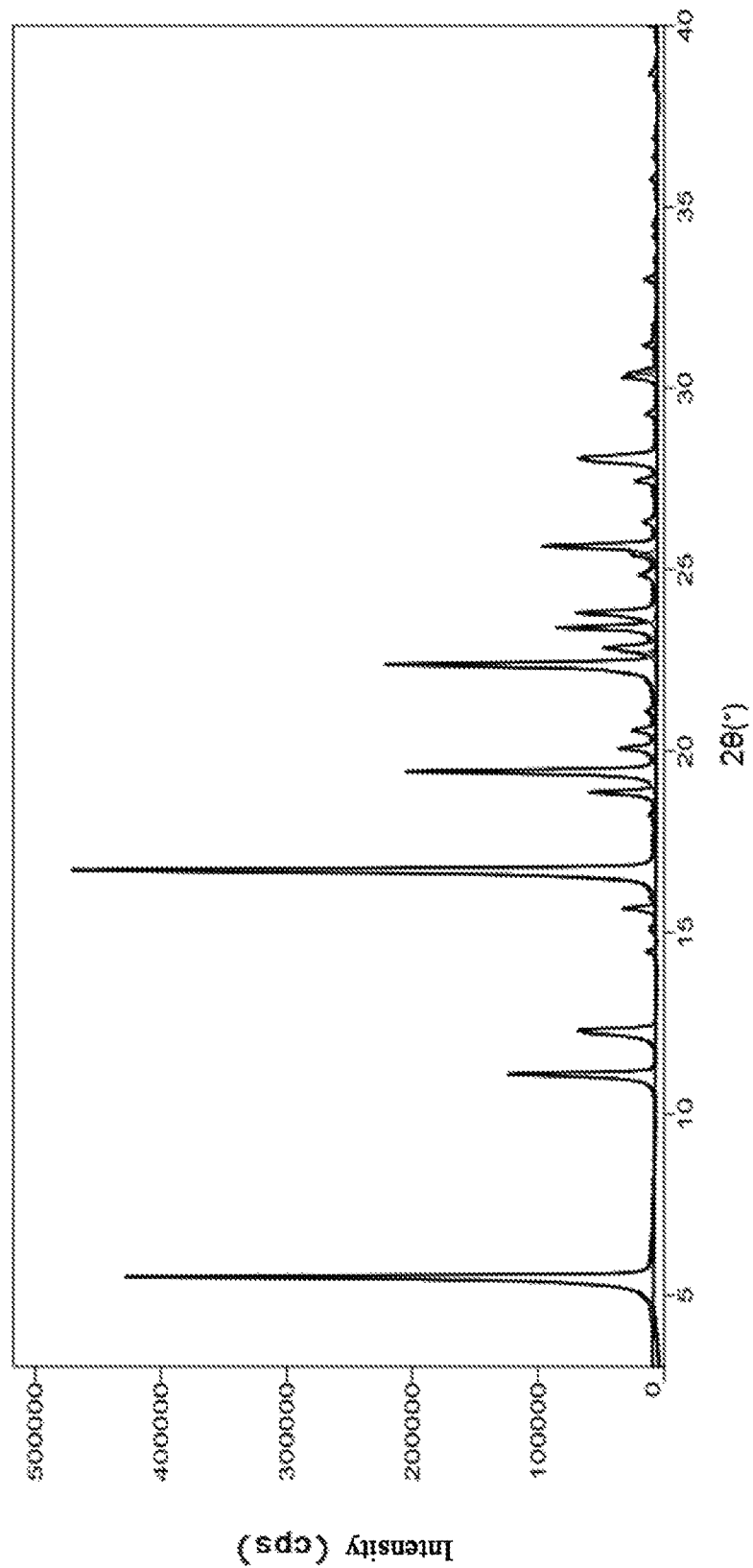
FIG. 3 shows the X-ray powder diffraction pattern of crystalline form A of the compound of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) of the present invention.
Figure 4:
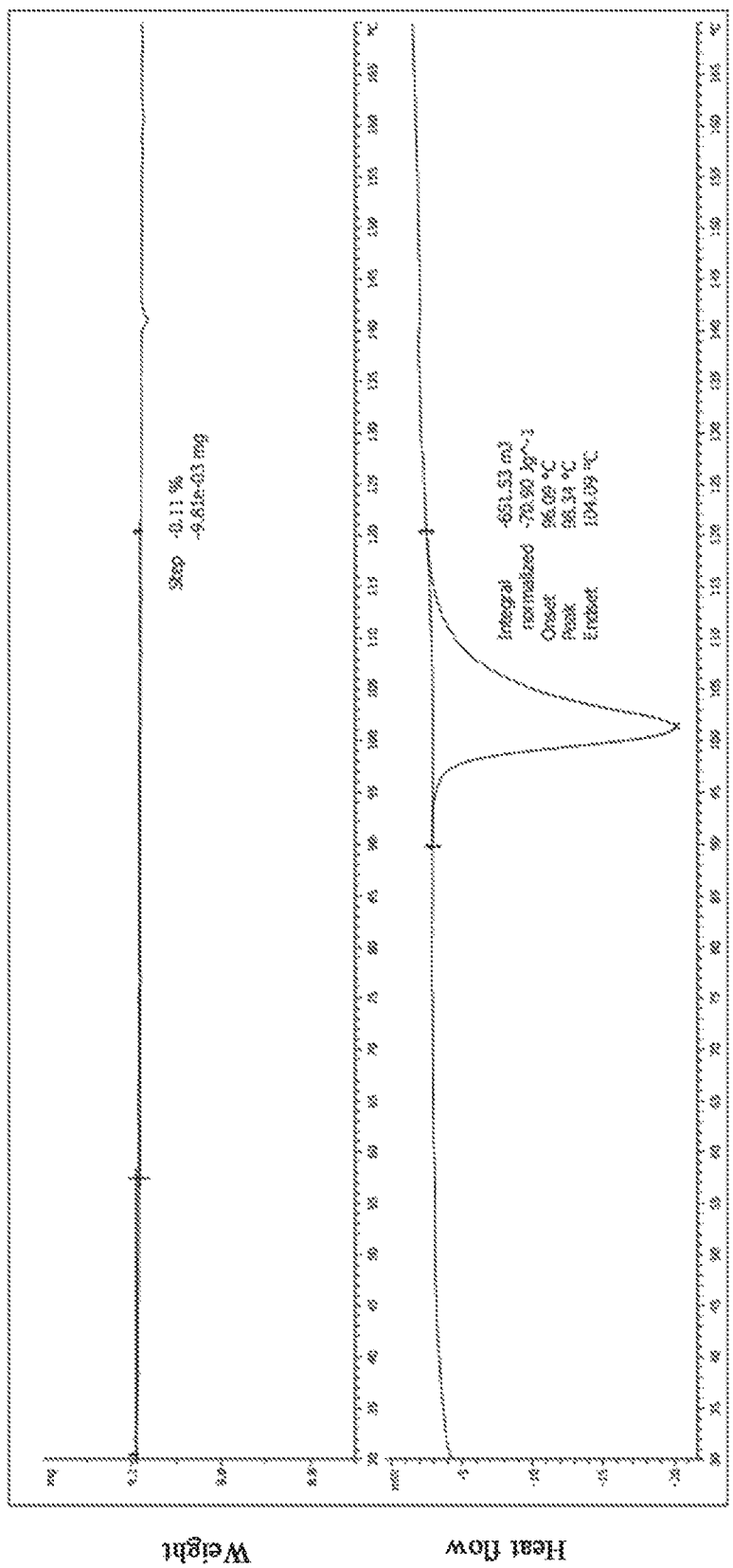
FIG. 4 shows the DSC-TGA pattern of crystalline form A of the compound of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) of the present invention.

The X-ray powder diffraction pattern and DSC-TGA pattern of this product are shown in FIG. 3 and FIG. 4, respectively. The product is crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2).

Example 18

Crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2)

To a reaction flask was added compound I-2 (3.00 g), and absolute methanol (10 mL) was added. The reaction mixture was heated to reflux to obtain a clear solution. The resulting solution was allowed to cool down to 20-25° C. and the temperature was maintained for 2 h for crystallization. The resulting mixture was filtered and dried under vacuum at 40-45° C. for 10 h to obtain a pale yellow solid (2.18 g, yield: 72.67%).

The resulting pale yellow solid was determined by X-ray powder diffraction and DSC-TGA as crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2).

Example 19

Crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2)

To a reaction flask was added compound I-2 (4.00 g), and acetic acid (6 mL) was added. The reaction mixture was heated to 80-100° C. to obtain a clear solution. The resulting solution was allowed to cool down to 20-25° C. and the temperature was maintained for 2 h for crystallization. The resulting mixture was filtered, the obtained solid was washed with absolute ethanol and then washed with n-hexane, and dried under vacuum at 40-45° C. for 10 h to obtain a pale yellow solid (2.85 g, yield: 71.25%).

Figure 5:
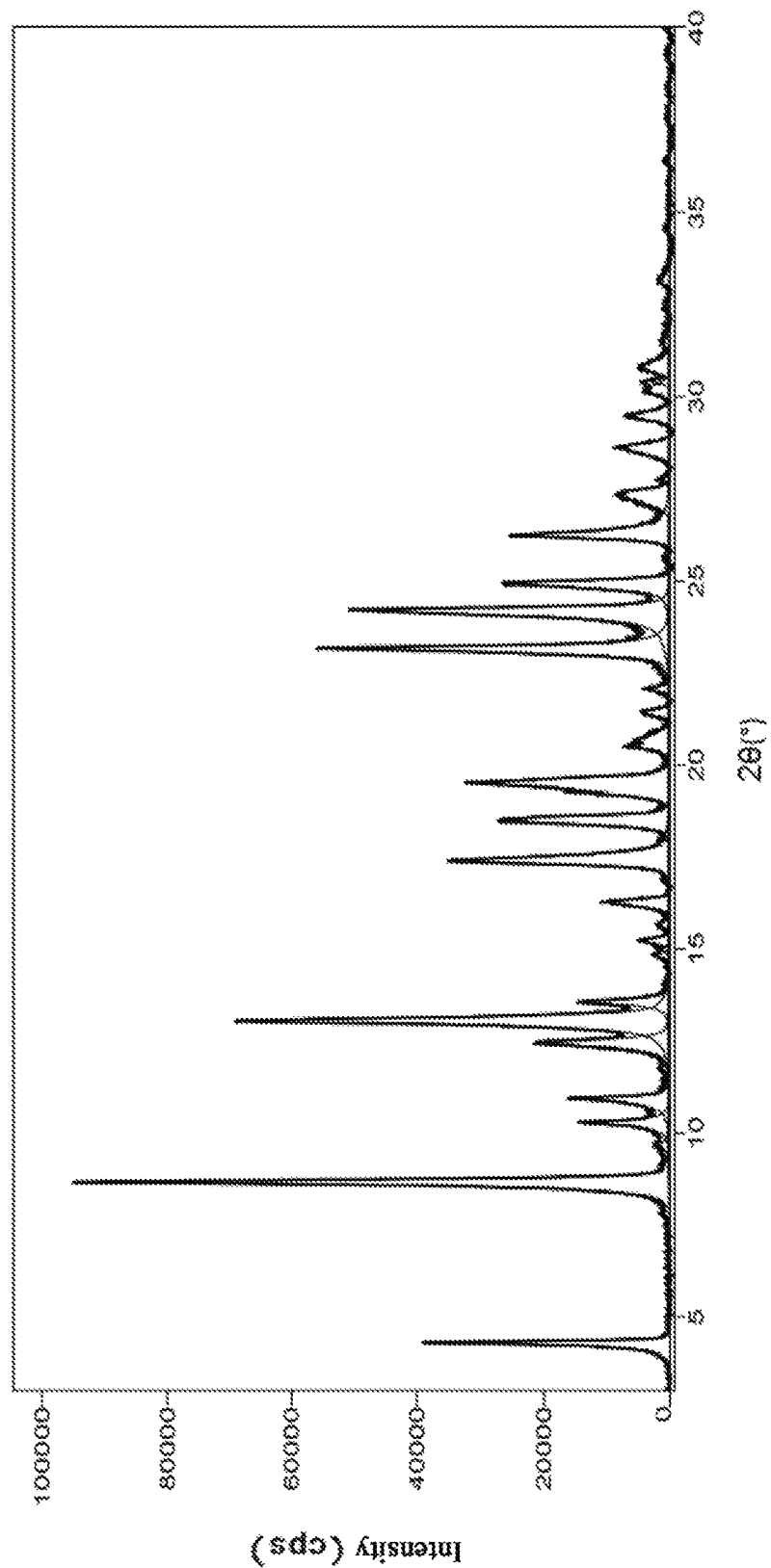
FIG. 5 shows the X-ray powder diffraction pattern of crystalline form B of the compound of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) of the present invention.
Figure 6:
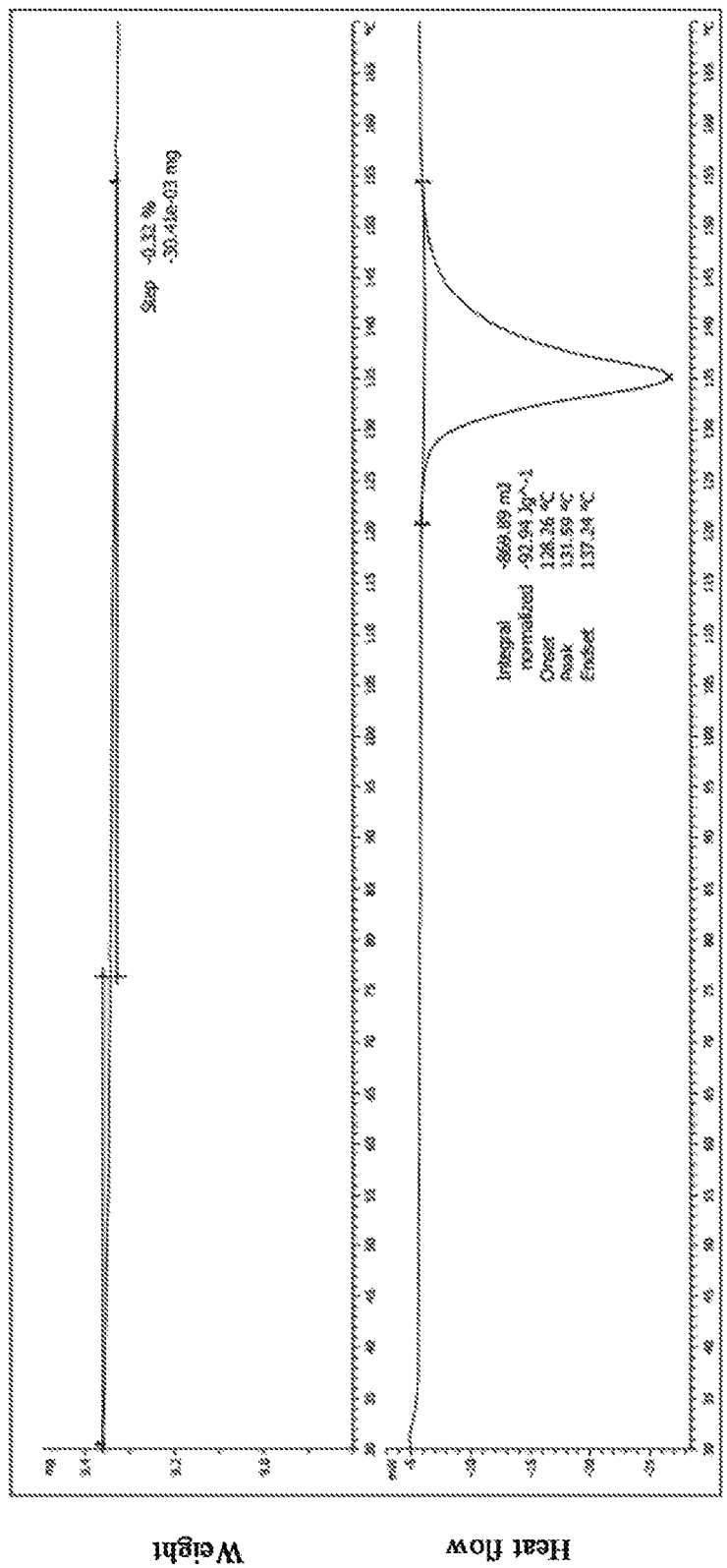
FIG. 6 shows the DSC-TGA pattern of crystalline form B of the compound of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) of the present invention.

The X-ray powder diffraction pattern and DSC-TGA pattern of this product are shown in FIG. 5 and FIG. 6, respectively. The product is crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2).

Example 20

Crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3)

To a reaction flask was added compound I-3 (3.00 g), and methanol (40 mL) was added. The reaction mixture was heated to reflux to obtain a clear solution. The resulting solution was allowed to cool down to 20-25° C. and the temperature was maintained for 3 h for crystallization. The resulting mixture was filtered and air-dried at 35-40° C. for 8 h to obtain a pale yellow solid (1.50 g, yield: 50.00%).

Figure 7:
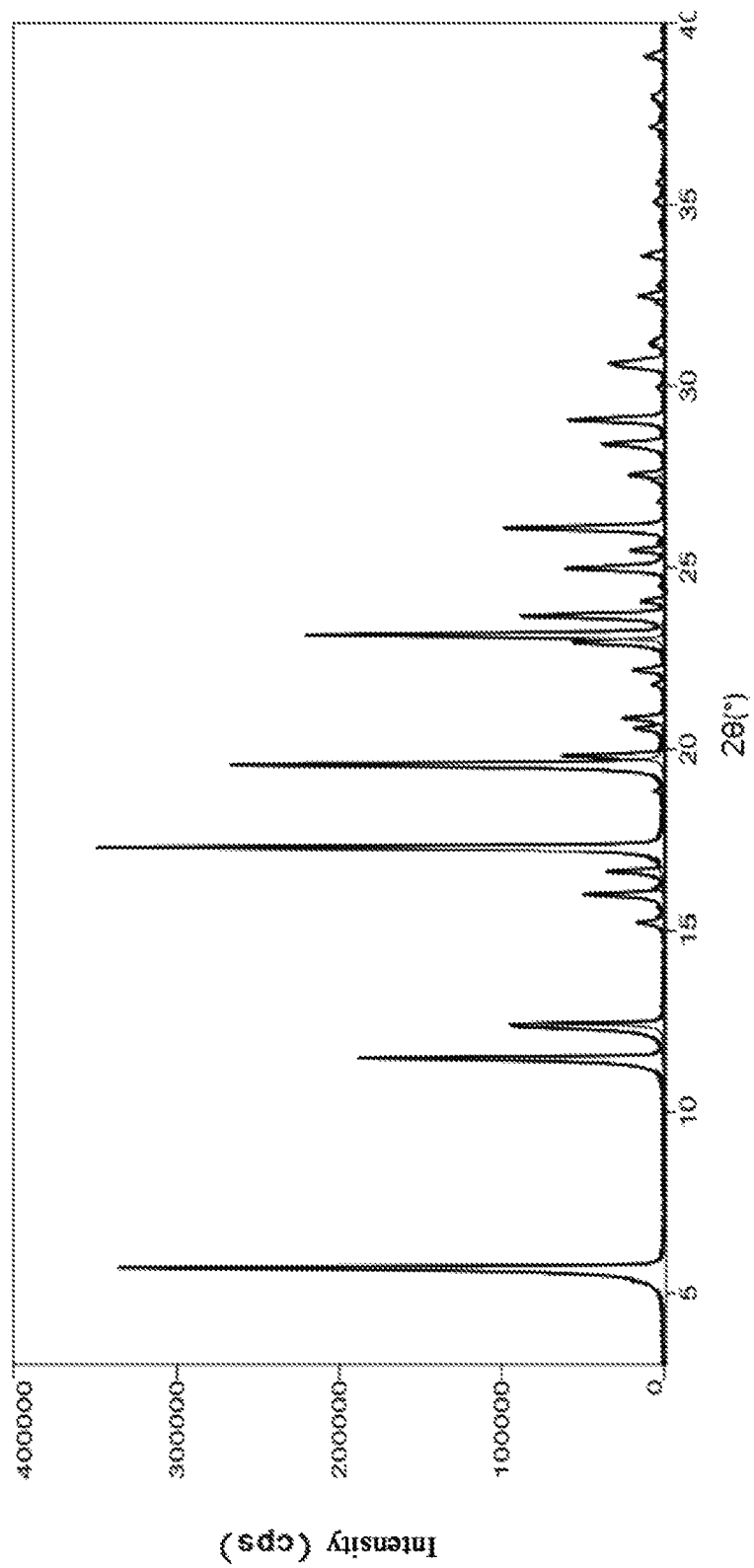
FIG. 7 shows the X-ray powder diffraction pattern of crystalline form A of the compound of methyl (S,E)-2-(2-chlorophenyl)-2-(2-(2,4-pentadienoyloxy)-6,7-dihydrothieno[3,2-c]pyridin-5(4H)-yl)-acetate (I-3) of the present invention.
Figure 8:
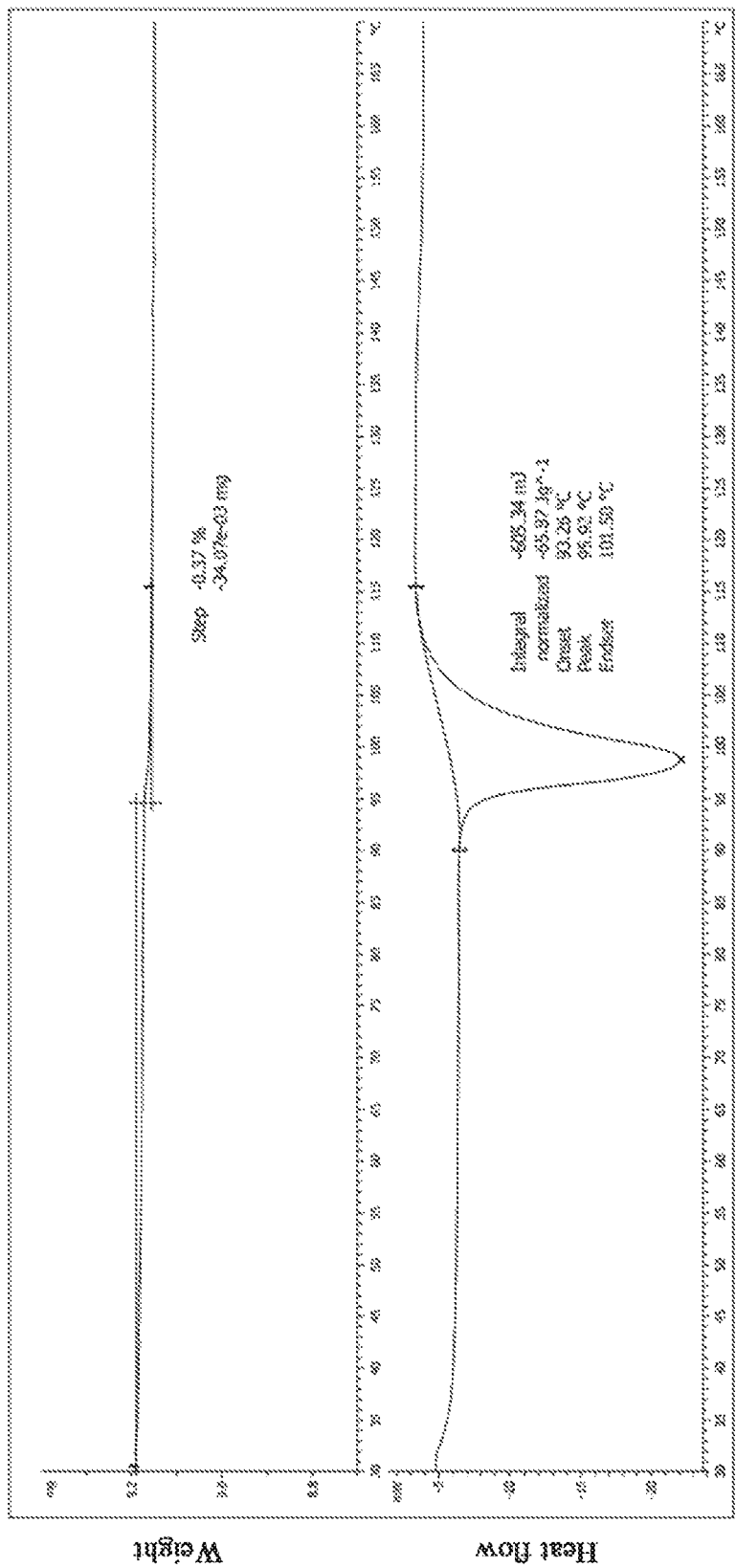
FIG. 8 shows the DSC-TGA pattern of crystalline form A of the compound of methyl (S,E)-2-(2-chlorophenyl)-2-(2-(2,4-pentadienoyloxy)-6,7-dihydrothieno[3,2-c]pyridin-5(4H)-yl)-acetate (I-3) of the present invention.

The X-ray powder diffraction pattern and DSC-TGA pattern of this product are shown in FIG. 7 and FIG. 8, respectively. The product is crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3).

Example 21

Crystalline form A of methyl (S,E)-2-(2-chlorophenyl)-2-(2-(2-pentenoyl-oxy)-6,7-dihydrothieno[3,2-c]pyridin-5(4H)-yl)-acetate (I-4)

To a reaction flask was added compound I-4 (3.00 g), and methanol (10 mL) was added. The reaction mixture was heated to reflux to obtain a clear solution. The resulting solution was allowed to cool down to 20-25° C. and the temperature was maintained for 4 h for crystallization. The resulting mixture was filtered and dried under vacuum at 40-45° C. for 6 h to obtain an off-white solid (2.50 g, yield: 83.33%).

Figure 9:
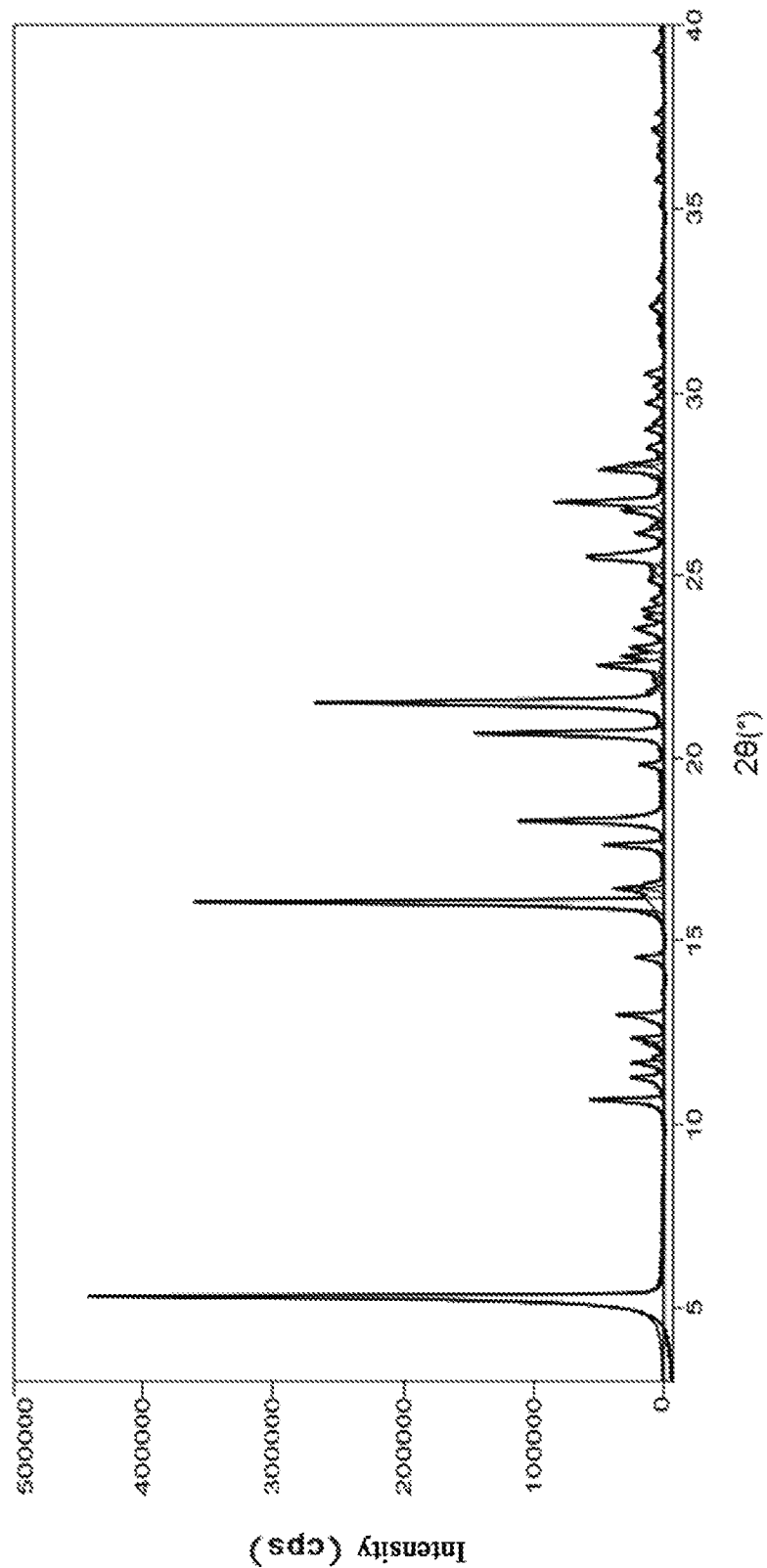
FIG. 9 shows the X-ray powder diffraction pattern of crystalline form A of the compound of methyl (S,E)-2-(2-chlorophenyl)-2-(2-(2-pentenoyloxy)-6,7-dihydrothieno[3,2-c]pyridin-5(4H)-yl)-acetate (I-4) of the present invention.
Figure 10:
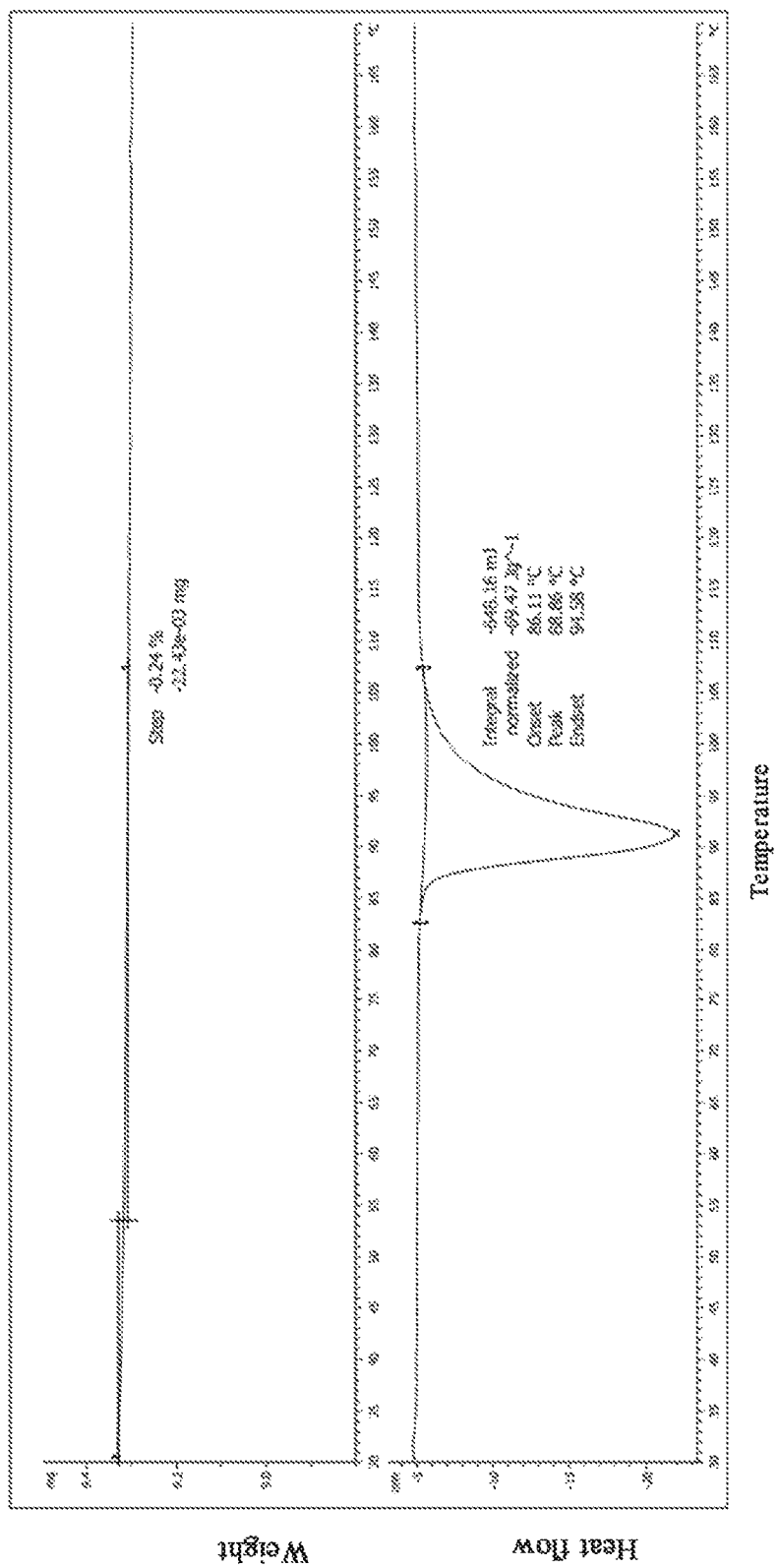
FIG. 10 shows the DSC-TGA pattern of crystalline form A of the compound of methyl (S,E)-2-(2-chlorophenyl)-2-(2-(2-pentenoyloxy)-6,7-dihydrothieno[3,2-c]pyridin-5(4H)-yl)-acetate (I-4) of the present invention.

The X-ray powder diffraction pattern and DSC-TGA pattern of this product are shown in FIG. 9 and FIG. 10, respectively. The product is crystalline form A of methyl (S,E)-2-(2-chlorophenyl)-2-(2-(2-pentenoyloxy)-6,7-dihydrothieno[3,2-c]pyridin-5(4H)-yl)-acetate (I-4).

Example 22

Crystalline form A of methyl (S,E)-2-(2-chlorophenyl)-2-(2-(2-hexenoyl-oxy)-6,7-dihydrothieno[3,2-c]pyridin-5(4H)-yl)-acetate (I-5)

To a reaction flask was added compound I-5 (4.00 g), and absolute ethanol (20 mL) was added. The reaction mixture was heated to reflux to obtain a clear solution. The resulting solution was allowed to cool down to 20-25° C. and the temperature was maintained for 4 h for crystallization. The resulting mixture was filtered and dried under vacuum at 40-45° C. for 6 h to obtain an off-white solid (3.20 g, yield: 80.00%).

Figure 11:
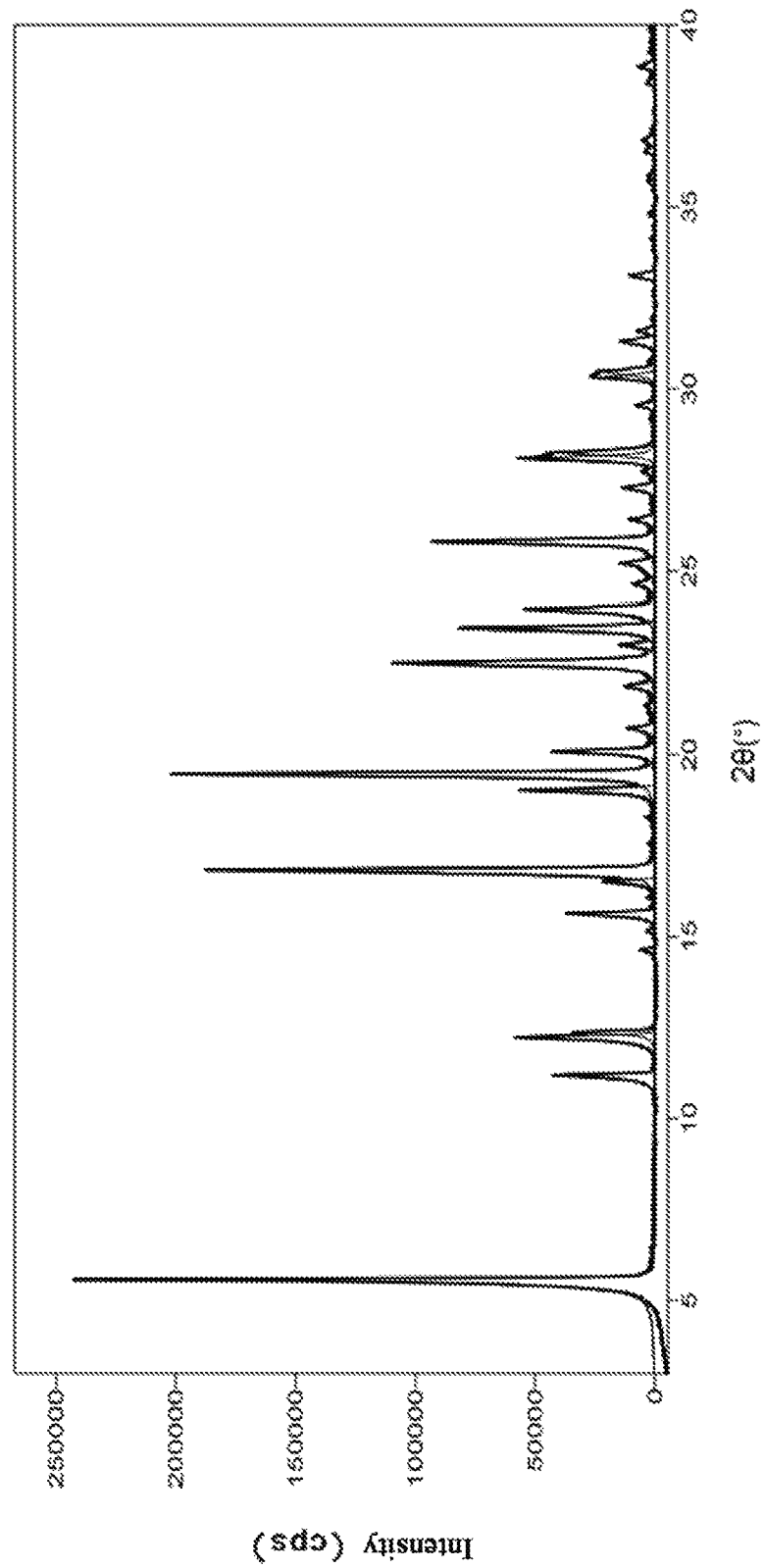
FIG. 11 shows the X-ray powder diffraction pattern of crystalline form A of the compound of methyl (S,E)-2-(2-chlorophenyl)-2-(2-(2-hexenoyloxy)-6,7-dihydrothieno[3,2-c]pyridin-5(4H)-yl)-acetate (I-5) of the present invention.
Figure 12:
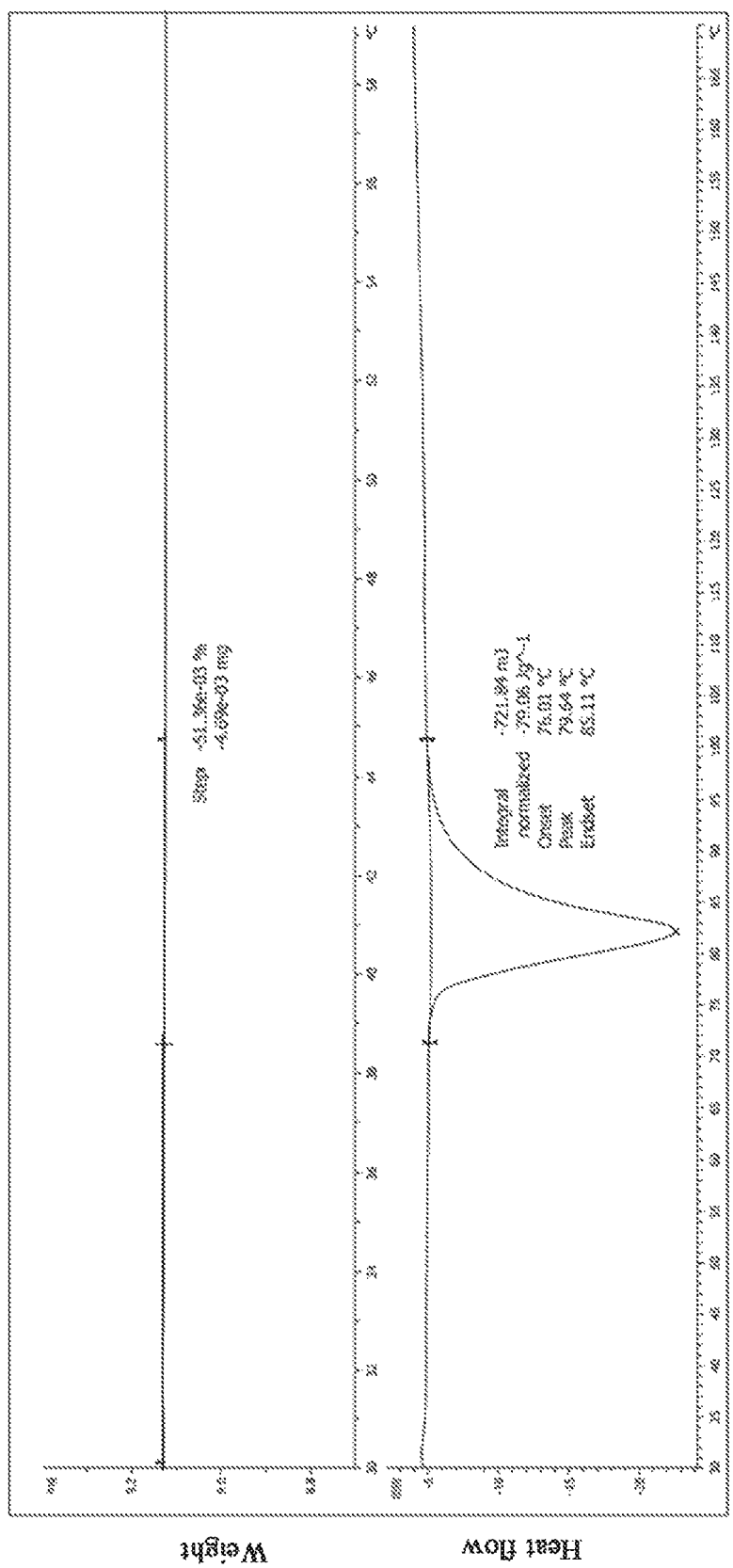
FIG. 12 shows the DSC-TGA pattern of crystalline form A of the compound of methyl (S,E)-2-(2-chlorophenyl)-2-(2-(2-hexenoyloxy)-6,7-dihydrothieno[3,2-c]pyridin-5(4H)-yl)-acetate (I-5) of the present invention.

The X-ray powder diffraction pattern and DSC-TGA pattern of this product are shown in FIG. 11 and FIG. 12, respectively. The product is crystalline form A of methyl (S,E)-2-(2-chlorophenyl)-2-(2-(2-hexenoyloxy)-6,7-dihydrothieno[3,2-c]pyridin-5(4H)-yl)-acetate (I-5).

Example 23

Test of Inhibitory Effect of Compounds on Platelet Aggregation in Rats

Healthy male SD rats were selected and randomly divided into solvent control group, positive drug control group and test compound group. Intragastric administration was carried out, with the administration volume being 10 ml/kg~bw. The solvent control group was administered an equal volume of 0.5% CMC-Na. 2 h after administration, the rats were anesthetized with 4.0% chloral hydrate (8.5 ml/kg) by intraperitoneal injection, blood was collected from the abdominal aorta, and 3.8% sodium citrate was used for anticoagulation. Platelet-rich plasma (PRP, 1100 rpm, centrifugated for 15 min) and platelet-poor plasma (PPP, 3500 rpm, centrifugated for 10 min) were routinely prepared. The platelet count was adjusted to $5 \times 10^8$ cells/ml with PPP. Along the wall of a platelet cuvette with a magnetic rotor was added well-mixed PRP (300 μL), which was incubated at 37° C. for 5 min, and then the maximum percentage of platelet aggregation induced by ADP (20 uM) was measured. The percentage inhibition of platelet aggregation of the test compounds and drugs was calculated, with the aggregation rate of the rats in the control group being 100%. All tests were completed within 2 h after blood collection, and the results are shown in Table 7.

TABLE 7

Inhibition of platelet aggregation after oral administration of test compounds to rats

| Group | Dose (mg/kg) | Sample size (number) | Aggregation rate (%) | Inhibition rate (%) | ED$_{50}$ (mg/kg) |
|---|---|---|---|---|---|
| Control | — | 6 | 60.0 ± 23.4 | — | — |
| Clopidogrel | 2.5 | 6 | 44.1 ± 13.5 | 26.5 | 4.130 |
|  | 5 | 6 | 24.2 ± 10.6** | 59.7 |  |
|  | 10 | 6 | 5.7 ± 7.5** | 90.5 |  |
| Prasugrel | 0.25 | 6 | 52.1 ± 6.6 | 13.3 | 0.612 |
|  | 0.5 | 6 | 37.4 ± 12.3* | 37.8 |  |
|  | 1 | 6 | 15.0 ± 10.2** | 75.0 |  |
| I-1 | 0.5 | 6 | 46.6 ± 8.1 | 22.4 | 1.004 |
|  | 1 | 6 | 29.9 ± 8.7** | 50.2 |  |
|  | 2 | 6 | 13.8 ± 11.7** | 77.0 |  |
| I-2 | 0.75 | 6 | 55.8 ± 13.9 | 7.0 | 1.582 |
|  | 1.5 | 6 | 29.6 ± 8.7** | 50.8 |  |
|  | 3 | 6 | 8.5 ± 9.4** | 85.8 |  |
| I-3 | 1 | 6 | 33.6 ± 31.3 | 44.0 | 1.043 |
|  | 2 | 6 | 1.44 ± 2.5** | 97.6 |  |
|  | 4 | 6 | 0.0 ± 0.0** | 100 |  |
| I-4 | 0.5 | 6 | 44.3 ± 25.8 | 26.2 | 1.266 |
|  | 1 | 6 | 37.1 ± 20.8 | 38.2 |  |
|  | 2 | 6 | 22.3 ± 17.2** | 62.9 |  |
|  | 4 | 6 | 13.0 ± 11.3** | 78.4 |  |
|  | 8 | 6 | 0.0 ± 0.0** | 100.0 |  |

TABLE 7-continued

Inhibition of platelet aggregation after oral
administration of test compounds to rats

| Group | Dose (mg/kg) | Sample size (number) | Aggregation rate (%) | Inhibition rate (%) | $ED_{50}$ (mg/kg) |
|---|---|---|---|---|---|
| I-5 | 0.5 | 6 | 48.4 ± 17.3 | 19.5 | 1.032 |
|  | 1 | 6 | 28.3 ± 11.7** | 52.8 |  |
|  | 2 | 6 | 15.4 ± 14.7** | 74.3 |  |

Note:
compared with the model group,
*$p < 0.05$;
**$p < 0.01$.

It can be seen from the test results that, compared with the normal control group, the compounds having the structure of formula (I) of the present invention have a significant effect against ADP-induced platelet aggregation. Therefore, they can be used to prevent or treat cardiovascular and cerebrovascular diseases such as coronary artery syndrome, myocardial infarction, and myocardial ischemia caused by platelet aggregation.

Example 24

Test of Effect of Compounds on Arteriovenous Bypass Thrombosis in Rats

Male SD rats were randomly divided into solvent control group, positive drug control group and test compound group. The solvent control group was administered a corresponding volume of the solvent. The test compound group was intragastrically administered with the test compounds at a dose of 1.0, 3.0, 10.0 and 30.0 mg/kg, respectively. The positive drug control group was intragastrically administered with prasugrel (0.1, 0.3, 1.0 and 3.0 mg/kg) or clopidogrel (3, 10 and 30 mg/kg). Rats were anesthetized with 4% chloral hydrate (0.32 g/kg), and fixed on the operating table at the supine position. The right common carotid artery and the left external jugular vein were separated, and was each inserted with a Teflon tube filled with normal saline solution containing heparin (50 U/mL), which were connected through another Teflon tube. A 6 cm long cotton thread was placed at the joints of the two tubes. After 2.5 h of administration, the arteriovenous loop was opened in each group and circulated for 15 min. The blood flow was interrupted, and the cotton thread wrapped with the thrombus was quickly removed and weighed. The weight of the cotton thread was subtracted to obtain the wet weight of the thrombus, and then it was baked in the oven to constant weight and weighed. The weight of the cotton thread was subtracted to obtain the dry weight of the thrombus.

The test results show that all of the test compounds can inhibit the thrombosis of arteriovenous bypass model in rats in a dose-dependent manner.

TABLE 8

Effects of compounds on dry weight of thrombus
from arteriovenous bypass in rats

| Group | Dose (mg/kg) | Dry weight of thrombus (%) | Inhibition rate (%) | $ED_{50}$ (mg/kg) |
|---|---|---|---|---|
| Model | — | 10.1 ± 1.9 | — |  |
| Prasugrel | 0.1 | 9.5 ± 2.4 | 6.0 | 1.571 |
|  | 0.3 | 9.2 ± 2.1 | 9.0 |  |
|  | 1 | 6.5 ± 2.0** | 35.7 |  |
|  | 3 | 3.0 ± 1.5** | 70.2 |  |
| Clopidogrel | 3 | 7.7 ± 1.2 | 24.2 | 11.845 |
|  | 10 | 5.9 ± 2.4** | 41.5 |  |
|  | 30 | 2.8 ± 1.5** | 72.6 |  |
| I-1 | 1 | 8.3 ± 2.7 | 18.3 | 7.888 |
|  | 3 | 5.8 ± 1.4** | 43.2 |  |
|  | 10 | 4.5 ± 2.4** | 56.0 |  |
|  | 30 | 3.6 ± 0.5** | 64.2 |  |
| I-2 | 1 | 6.4 ± 3.6 | 36.5 | 5.861 |
|  | 3 | 6.1 ± 2.9* | 40.3 |  |
|  | 10 | 4.9 ± 2.3** | 52.1 |  |
|  | 30 | 3.2 ± 1.5** | 68.6 |  |

Note:
compared with the model group,
*$p < 0.05$;
**$p < 0.01$

Example 25

Study on pharmacokinetics of compounds: clopidogrel is a prodrug which requires two steps of metabolism in vivo to be converted into an active metabolite. The steps are as follows:

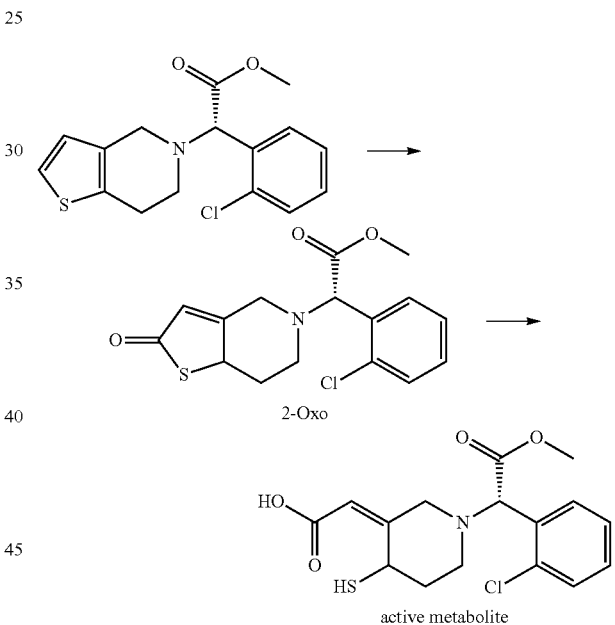

2-Oxo active metabolite

Studies have shown that there is gene polymorphism in human CYP2C19, which mainly affects the first-step metabolism of clopidogrel, and a considerable proportion of the population has a relatively low metabolism of clopidogrel. It is reported by literatures that the genetic mutation rates in Japanese, Asians, Australians, Caucasians, and African-Americans were 28%, 30%, 35%, 13%, and 18%, respectively, and this portion of population is prone to develop "clopidogrel resistance", and thus being prone to occur severe cardiovascular and cerebrovascular events. Therefore, whether the relevant drug can be successfully metabolized into 2-oxo (2-Oxo) product in plasma can indicate whether the drug can solve the problem of "drug resistance".

Plasma samples (double sample) containing 1 µM of the compounds of the present invention, clopidogrel hydrogen sulfate (LBGL), 2-oxo product (2-Oxo) were prepared from human blank plasma, and incubated at 37° C. 50 µL of the above incubated plasma samples were taken at different time points, and 100 μL of precipitant (acetonitrile:methanol=7:3) and 50 μL of internal standard were added. The mixture was vortexed for 1 min and centrifuged for 10 min. 100 μL of the supernatant was taken into an inner inserted tube, centrifuged for 5 min, and injected for LC-MS/MS analysis.

Preparation of blank control sample (PPT-0): 100 μL of frozen human blank plasma was taken, to which 195 μL of acetonitrile and 100 μL of internal standard were added, followed by 5 μL of the compound of the present invention, clopidogrel or 2-oxo product (20 μM). The mixture was vortexed for 1 min and centrifuged for 10 min. 100 μL of the supernatant was taken into an inner inserted tube, centrifuged for 5 min, and injected for LC-MS/MS analysis. The results are shown in Table 9-11:

TABLE 9

Clopidogrel and metabolite concentrations in human plasma at different time points of incubation

| Time | LBGL | |
|---|---|---|
| (min) | μM | % |
| 0 | 0.965 | 98.1 |
| 5 | 1.045 | 106 |
| 10 | 1.000 | 102 |
| 20 | 0.987 | 100 |
| 30 | 1.025 | 104 |
| 45 | 0.995 | 101 |
| 60 | 0.981 | 100 |
| 90 | 0.924 | 94.0 |
| 120 | 0.944 | 96.0 |

TABLE 10

I-1 and metabolite concentrations in human plasma at different time points of incubation

| Time | I-1 | | 2-Oxo | |
|---|---|---|---|---|
| (min) | μM | % | μM | % |
| 0 | 0.950 | 100 | 0.0412 | 4.34 |
| 5 | 0.872 | 91.7 | 0.0807 | 8.49 |
| 10 | 0.782 | 82.3 | 0.143 | 15.1 |
| 20 | 0.575 | 60.5 | 0.195 | 20.5 |
| 30 | 0.425 | 44.7 | 0.198 | 20.8 |
| 45 | 0.266 | 28.0 | 0.167 | 17.5 |
| 60 | 0.174 | 18.3 | 0.130 | 13.6 |
| 90 | 0.0522 | 5.49 | 0.0535 | 5.63 |
| 120 | 0.0162 | 1.70 | 0.0224 | 2.35 |
| 150 | 0.00531 | 0.558 | 0.00857 | 0.902 |
| 180 | 0.00219 | 0.231 | 0.00397 | 0.418 |
| 240 | 0 | 0 | 0 | 0 |
| 300 | 0 | 0 | 0 | 0 |
| 360 | 0 | 0 | 0 | 0 |

TABLE 11

I-2 and metabolite concentrations in human plasma at different time points of incubation

| Time | I-2 | | 2-Oxo | |
|---|---|---|---|---|
| (min) | μM | % | μM | % |
| 0 | 1.11 | 100 | 0.0192 | 1.74 |
| 5 | 1.03 | 93.5 | 0.0246 | 2.23 |
| 10 | 1.03 | 92.8 | 0.0319 | 2.89 |
| 20 | 1.07 | 97.1 | 0.0449 | 4.06 |
| 30 | 0.957 | 86.6 | 0.0493 | 4.46 |
| 45 | 0.927 | 83.9 | 0.0522 | 4.72 |
| 60 | 0.849 | 76.8 | 0.0521 | 4.71 |
| 90 | 0.705 | 63.8 | 0.0481 | 4.35 |
| 120 | 0.695 | 62.9 | 0.0457 | 4.14 |
| 150 | 0.516 | 46.7 | 0.0445 | 4.03 |
| 180 | 0.475 | 43.0 | 0.0388 | 3.51 |
| 240 | 0.332 | 30.0 | 0.0331 | 3.00 |
| 300 | 0.231 | 20.9 | 0.0294 | 2.66 |
| 360 | 0.164 | 14.8 | 0.0236 | 2.14 |

It can be seen from the test results that clopidogrel is substantially stable in human plasma over 120 min; the representative compounds I-1 and I-2 of the present invention rapidly generate 2-oxo products in human plasma.

The test results show that the compounds of the formula (I) of the present invention are not affected by gene polymorphism of the CYP2C19, and can be rapidly metabolized into a 2-oxo (2-Oxo) product in the plasma, which can solve the problem of "clopidogrel resistance".

Example 26

Safety Test:

Safety Evaluation of Compounds I-1 and I-2 in Single Dosing:

The test consisted of a physiological control group, a solvent control group, and two administration groups, with 4 animals in each group, half of which were male and the other half of which were female. The animals were intragastrically administered with the test compounds at a single dose of 2 g/kg. The solvent control group was administered with an equal volume of the blank solvent. Animals were daily observed for various conditions during the test. ECG examinations were performed before administration, 1 h after administration, and 7 and 14 days after administration. Hematological and blood biochemical tests were performed before administration and 1, 7 and 12 days after administration.

The animals had normal activities, good mental condition, and normal diet during the administration and observation period after the administration. There were no obvious abnormalities in the ECG examinations, hematological tests and serum biochemical tests.

It was reported by the literature that in the acute toxicity test of prasugrel in dog, toxic effects such as vomiting, increased ALP, and decreased platelet aggregation etc. occurred at a dose of ≥300 mg/kg, and toxic effect such as vomiting etc. occurred at a dose of 1000 mg/kg, and toxic effect such as hepatocellular atrophy etc. occurred at a dose of 2000 mg/kg.

It can be known that the compounds of the present invention are less toxic to beagle dogs, which have no toxic response to a high dose of administration, and the compounds have higher safety.

Safety Evaluation of Compounds I-1 and I-2 in Multiple Dosing:

The test consisted of a physiological control group, a solvent control group, and two administration groups, with 4 animals in each group, half of which were male and the other half of which were female. Two dose groups, 100 mg/kg group and 300 mg/kg group, were set for the test compounds, to which the test compounds at doses of 100 mg/kg and 300 mg/kg were intragastrically administered respectively over 14 days. The solvent control group was administered with an equal volume of the blank solvent. Animals were daily observed for various conditions during the test. ECG examinations were performed before administration, and 7 and 14 days after administration. Hematological and blood biochemical tests were performed before administration and 7 and 15 days after administration.

100 mg/kg dose group: the animals had normal activities, good mental condition, and normal diet after the administration. There were no obvious abnormalities in the ECG examinations, hematological tests and serum biochemical tests on day 7 and 14 after administration.

300 mg/kg dose group: the animals had normal activities, good mental condition, and normal diet after the administration. There were no obvious abnormalities in the ECG examinations, hematological tests and serum biochemicals test on day 7 and 14 after administration.

The test results showed that continuous intragastrical administration of the representative compounds I-1 and I-2 of the present invention for 14 days showed no significant drug-related toxicity in appearance, mental activity, appetite and several examinations such as hematological, blood biochemical, and ECG etc. examinations in beagle dogs. No abnormal phenomena such as mydriasis and vomiting etc. was observed, no signs of hepatotoxicity such as elevated ALP and ALT etc. was observed, and no other abnormal toxicities were observed.

It was reported by the literature that in the multiple dosing test of prasugrel in dog over two weeks, toxic responses such as mydriasis, vomiting, white matter (unabsorbed test substance) in stool, decreased platelet aggregation, increased ALP, increased total liver volume, hepatocyte swelling, hyaline surface and testicular seminiferous epithelial atrophy etc. occurred at a dose of ≥100 mg/kg/day, and toxic response such as weight loss etc. also occurred at a dose of ≥300 mg/kg/day.

It can be known that the compounds having the structure of formula (I) of the present invention are less toxic to beagle dogs when administered intragastrically, and have higher safety.

Example 27

Test of Hemorrhagic Side Effects:

Healthy male SD rats were selected and randomly divided into model control group, prasugrel group, and test compound group, and intragastrical administration was carried out. 1 h after administration, the rats were anesthetized by intraperitoneal injection of 20% urethane (1 g/kg), and the tail was cut off 5 mm from the tip of the tail, which was then placed in a test tube containing 5 ml normal saline at 37° C. The time from tail cut to cease of bleeding was recorded as the bleeding time. The increasing rate of bleeding time in each dose group was calculated, with the bleeding time of the rats in the control group being 100%. A linear equation was fitted to calculate the dose of prasugrel and the compound of the present invention that doubled the bleeding time ($ED_{200}$).

TABLE 12

Effects of prasugrel and compound of the present invention on bleeding time of amputated tail in rats

| Compound | $ED_{200}$ (mg·kg$^{-1}$) |
|---|---|
| Prasugrel | 0.513 |
| I-1 | 1.977 |

It can be known from the test results that the compounds having the structure of formula (I) of the present invention have a significantly lower hemorrhagic risk than prasugrel.

Example 28

Study on the Stability of the Compounds:

The stability of the compound is investigated under the conditions of high temperature, high humidity and light. The testing conditions for high performance liquid chromatography (HPLC) are as follows:

Method 1:
Instrument: high performance liquid chromatography;
Column: Inertsil C8-3, 150 mm×4.6 mm, 5 μm;
Mobile phase A: acetonitrile; mobile phase B: 5 mM ammonium dihydrogen phosphate;
Flow rate: 1.0 mL/min;
Detection wavelength: 220 nm;
Running time: 60 min;
Injection volume: 20 μL;
Column temperature: 35° C.;
Sample chamber temperature: 25° C.;
Gradient elution table:

TABLE 13

Gradient elution list

| Time (min) | Mobile phaseA (%) | Mobile phaseB (%) |
|---|---|---|
| 0 | 45 | 55 |
| 30 | 60 | 40 |
| 45 | 70 | 30 |
| 50 | 80 | 20 |
| 55 | 80 | 20 |
| 56 | 45 | 55 |
| 60 | 45 | 55 |

Method 2:
Column: Agilent Poroshell 120 EC-C18, 100 mm×4.6 mm, 2.7 μm;
Column temperature: 30° C.;
Other conditions are the same as that in Method 1.

Samples relating to Compound I-2 were tested using Method 2 and other samples were tested using Method 1. The test results of the influence factors are shown in Table 14, and the test results of the light-avoidance stability test are shown in Table 15.

TABLE 14

Data list of influence factors results of compounds

| Compound | Test item | 0 day 0point | 5 days High temperature 60° C. | 5 days Light 4500 ± 500 LX | 5 days High humidity RH92.5% | 10 days High temperature 60° C. | 10 days Light 4500 ± 500 LX | 10 days High humidity RH92.5% | 30 days High temperature 60° C. | 30 days Light 4500 ± 500 LX | 30 days High humidity RH92.5% |
|---|---|---|---|---|---|---|---|---|---|---|---|
| I-1 | Appearance | White solid | White solid | White solid | White solid | White solid | White solid | White solid | White solid | Pale yellow solid | White solid |

TABLE 14-continued

Data list of influence factors results of compounds

| Compound | Test item | 0 day 0point | 5 days High temperature 60° C. | 5 days Light 4500 ± 500 LX | 5 days High humidity RH92.5% | 10 days High temperature 60° C. | 10 days Light 4500 ± 500 LX | 10 days High humidity RH92.5% | 30 days High temperature 60° C. | 30 days Light 4500 ± 500 LX | 30 days High humidity RH92.5% |
|---|---|---|---|---|---|---|---|---|---|---|---|
| | Individual maximum impurity % | 0.236 | 0.234 | 0.287 | 0.235 | 0.232 | 0.313 | 0.234 | 0.237 | 0.698 | 0.235 |
| | Chromatographic purity % | 99.612 | 99.595 | 99.539 | 99.583 | 99.596 | 99.502 | 99.578 | 99.570 | 98.868 | 99.544 |
| I-2 | Appearance | Pale yellow solid | Pale yellow solid | Pale yellow solid | Pale yellow solid | Pale yellow solid | Yellow solid | Pale yellow solid | Yellow solid | Ocherous solid | Pale yellow solid |
| | Isomer % | 0.705 | 0.696 | 0.699 | 0.707 | 0.692 | 0.712 | 0.708 | 0.683 | 0.695 | 0.704 |
| | Chromatographic purity % | 98.879 | 98.840 | 98.853 | 98.897 | 98.930 | 98.756 | 98.882 | 98.936 | 95.099 | 98.885 |
| D-8 | Appearance | Pale orange solid | Pale brown solid | Brown solid | Pale orange solid | Brown solid | Brown solid | Pale orange solid | Black block | Red Brown Solid | Pale orange solid |
| | Individual maximum impurity % | 0.135 | 0.510 | 1.094 | 0.127 | 1.224 | 2.821 | 0.104 | 5.418 | 8.206 | 0.172 |
| | Chromatographic purity % | 99.118 | 96.953 | 91.635 | 99.253 | 93.371 | 80.960 | 99.202 | 80.070 | 59.908 | 98.933 |
| D-9 | Appearance | White solid | Brown solid | Pale yellow solid | Brown oil | Brown solid | Pale yellow solid | Brown oil | Brown solid | Pale yellow solid | Brown solid |
| | Individual maximum impurity % | 0.062 | 2.897 | 0.946 | 20.760 | 5.254 | 1.621 | 26.942 | 9.740 | 3.728 | 52.717 |
| | Chromatographic purity % | 99.802 | 92.725 | 97.637 | 29.362 | 84.395 | 96.472 | 3.827 | 39.866 | 91.198 | — |

TABLE 15

Data list for stability test of compounds after being packaged with aluminum foil

| Compound | Test item | 0 day 0 point | 5 days Light (aluminum foil) 4500 ± 500 LX | 10 days Light (aluminum foil) 4500 ± 500 LX | 30 days Light (aluminum foil) 4500 ± 500 LX |
|---|---|---|---|---|---|
| I-1 | Appearance | White solid | White solid | White solid | White solid |
| | Individual maximum impurity % | 0.236 | 0.242 | 0.243 | 0.242 |
| | Chromatographic purity % | 99.612 | 99.598 | 99.565 | 99.555 |
| I-2 | Appearance | Pale yellow solid | Pale yellow solid | Pale yellow solid | Pale yellow solid |
| | Individual maximum impurity % | 0.705 | 0.699 | 0.699 | 0.696 |
| | Chromatographic purity % | 98.879 | 98.348 | 98.544 | 98.434 |

The results show that compared with zero point the individual maximum impurity and chromatographic purity of the representative compounds of the present invention have not changed significantly under high temperature and high humidity conditions, indicating that the compounds have a good stability. Only slight degradation occurred under light conditions, which can be avoided by keeping away from light. However, the representative compounds reported by literatures have significantly reduced chromatographic purities under the conditions of high temperature, high humidity and light, and have poor stability.

Example 29

Study on the Stability of Crystalline Form A of methyl(S,E)-2-(2-chloro-phenyl)-2-(2-(2-butenoyloxy)-6,7-dihydrothieno[3,2-c]pyridin-5(4H)-yl)-acetate (I-1)

The stability of crystalline form A of methyl (S,E)-2-(2-chlorophenyl)-2-(2-(2-butenoyloxy)-6,7-dihydrothieno[3,2-c]pyridin-5 (4H)-yl)-acetate (I-1) was investigated under high temperature, high humidity and light conditions for 5 days, 10 days and 30 days. The results show that compared with zero point, the compound has good stability. At the same time, the X-ray powder diffraction analysis of the samples after investigation show that the crystalline form has not changed and is still crystalline form A, and the results show that the crystalline form is stable.

TABLE 16

Investigation on the stability of crystalline form

| Time point | | Crystalline form |
|---|---|---|
| 0 day | | Crystalline form A |
| 5 days | High humidity (RH 92.5%) | Crystalline form A |
| | High temperature (60° C.) | Crystalline form A |
| | Light (5000 ± 5000 Lx) | Crystalline form A |

TABLE 16-continued

Investigation on the stability of crystalline form

| | Time point | Crystalline form |
|---|---|---|
| 10 days | High humidity (RH 92.5%) | Crystalline form A |
| | High temperature (60° C.) | Crystalline form A |
| | Light (5000 ± 500 Lx) | Crystalline form A |
| 30 days | High humidity (RH 92.5%) | Crystalline form A |
| | High temperature (60° C.) | Crystalline form A |
| | Light (5000 ± 500 Lx) | Crystalline form A |

The invention claimed is:

1. A compound having a structure of formula (I):

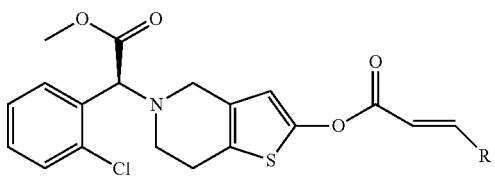

wherein R is methyl, ethyl, propyl, vinyl or propenyl.

2. The compound according to claim 1, which is selected from the following compounds:

I-1: methyl (S,E)-2-(2-chlorophenyl)-2-(2-(2-butenoyloxy)-6,7-dihydrothieno[3,2-c]pyridin-5(4H)-yl)-acetate;

I-2: methyl (S)-2-(2-chlorophenyl)-2-(2-((2E,4E)-2,4-hexadienoyloxy)-6,7-dihydrothieno[3,2-c]pyridin-5(4H)-yl)-acetate;

I-3: methyl (S,E)-2-(2-chlorophenyl)-2-(2-(2,4-pentadienoyloxy)-6,7-dihydrothieno[3,2-c]pyridin-5(4H)-yl)-acetate;

I-4: methyl (S,E)-2-(2-chlorophenyl)-2-(2-(2-pentenoyloxy)-6,7-dihydrothieno[3,2-c]pyridin-5(4H)-yl)-acetate; and I-5: methyl (S,E)-2-(2-chlorophenyl)-2-(2-(2-hexenoyloxy)-6,7-dihydrothieno[3,2-c]pyridin-5(4H)-yl)-acetate.

3. A method for preparing the compound having the structure of formula (I) according to claim 1, comprising the steps of:

reacting a compound having a structure of formula (II) with a corresponding acid, acyl chloride or acid anhydride in the presence of a base to prepare the compound having the structure of formula (I), wherein R is as defined in claim 1:

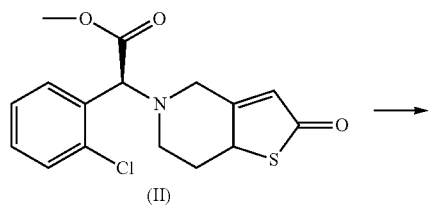

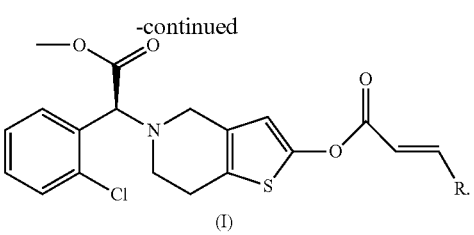

4. The method according to claim 3, wherein the compound having the structure of formula (II) is prepared by reacting a compound having a structure of formula (III) with a compound having a structure of formula (IV) in the presence of a base:

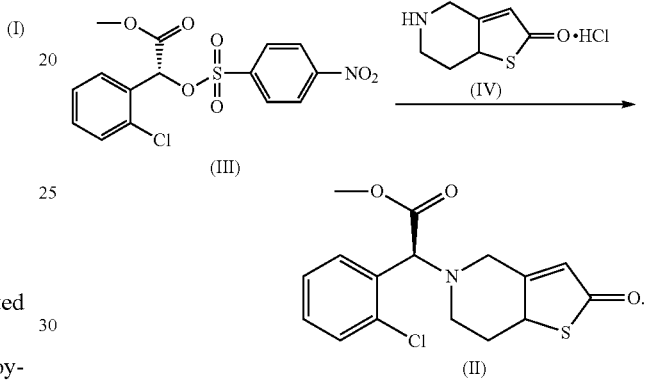

5. A pharmaceutical composition comprising the compound having the structure of formula (I) according to claim 1 and a pharmaceutically acceptable carrier or excipient.

6. The pharmaceutical composition according to claim 5, wherein said pharmaceutical composition is a solid oral preparation, a liquid oral preparation, or an injection.

7. The compound according to claim 1, which is a crystalline form A of methyl (S,E)-2-(2-chlorophenyl)-2-(2-(2-butenoyloxy)-6,7-dihydrothieno[3,2-c]pyridin-5(4H)-yl)-acetate (I-1), wherein said crystalline form A has an X-ray powder diffraction pattern having diffraction peaks at 5.31, 16.13, 20.24 and 21.58 expressed by 2θ degree using Cu-Kα radiation, with a 2θ angle measurement error being ±0.2.

8. The crystal form A according to claim 7, characterized in that, said crystalline form A has an X-ray powder diffraction pattern having diffraction peaks at 5.31, 10.70, 12.43, 16.13, 17.47, 20.24, 21.58, 25.83 and 27.09 expressed by 2θ degree using Cu-Kα radiation, with a 2θ angle measurement error being ±0.2.

9. A pharmaceutical composition comprising the crystalline form A of methyl (S,E)-2-(2-chlorophenyl)-2-(2-(2-butenoyloxy)-6,7-dihydrothieno[3,2-c]pyridin-5(4H)-yl)-acetate (I-1) according to claim 7 and a pharmaceutically acceptable carrier or excipient.

10. The pharmaceutical composition according to claim 9, wherein said pharmaceutical composition is a solid oral preparation, a liquid oral preparation, or an injection.

11. The compound according to claim 1, which is a crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), wherein said crystalline form A has an X-ray powder diffraction pattern having diffraction peaks at 5.52, 16.73, 19.43 and 22.38 expressed by 2θ degree using Cu-Ka radiation, with a 2θ angle measurement error being 0.2.

12. The crystal form A according to claim 11, characterized in that, said crystalline form A has an X-ray powder diffraction pattern having diffraction peaks at 5.52, 11.10, 12.30, 16.73, 18.86, 19.43, 22.38, 23.40 and 23.80 expressed by 2θ degree using Cu-Ka radiation, with a 2θ angle measurement error being ±0.2.

13. A pharmaceutical composition comprising the crystalline form A of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) according to claim 11 a pharmaceutically acceptable carrier or excipient.

14. The pharmaceutical composition according to claim 13, wherein said pharmaceutical composition is a solid oral preparation, a liquid oral preparation, or an injection.

15. The compound according to claim 1, which is a crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2), wherein said crystalline form B has an X-ray powder diffraction pattern having diffraction peaks at 4.31, 8.66, 13.01, 17.42 and 19.52 expressed by 2θ degree using Cu-Ka radiation, with a 2θ angle measurement error being 0.2.

16. The crystal form B according to claim 15, characterized in that, said crystalline form B has an X-ray powder diffraction pattern having diffraction peaks at 4.31, 8.66, 10.29, 10.94, 13.01, 17.42, 19.52, 23.17, 24.22 and 24.92 expressed by 2θ degree using Cu-Ka radiation, with a 2θ angle measurement error being ±0.2.

17. A pharmaceutical composition comprising the crystalline form B of methyl (S)-2-(2-chlorophenyl)-2-(2-((2E,4E)-2,4-hexadienoyloxy)-6,7-dihydrothieno[3,2-c]pyridin-5(4H)-yl)-acetate (I-2) according to claim 15 and a pharmaceutically acceptable carrier or excipient.

18. The pharmaceutical composition according to claim 17, wherein said pharmaceutical composition is a solid oral preparation, a liquid oral preparation, or an injection.

19. The compound according to claim 1, which is a crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3), wherein said crystalline form A has an X-ray powder diffraction pattern having diffraction peaks at 5.71, 11.49, 17.28, 19.57 and 23.14 expressed by 2θ degree using Cu-Ka radiation, with a 2θ angle measurement error being ±0.2.

20. The crystalline form A according to claim 19, characterized in that, said crystalline form A has an X-ray powder diffraction pattern having diffraction peaks at 5.71, 11.49, 12.43, 15.95, 16.56, 17.28, 19.57, 23.14, 23.66, 24.98 and 26.09 expressed by 2θ degree using Cu-Ka radiation, with a 2θ angle measurement error being ±0.2.

21. A pharmaceutical composition comprising the crystalline form A of methyl (S,E)-2-(2-chlorophenyl)-2-(2-(2,4-pentadienoyloxy)-6,7-dihydrothieno[3,2-c]pyridin-5(4H)-yl)-acetate (I-3) according to claim 19 and a pharmaceutically acceptable carrier or excipient.

22. The pharmaceutical composition according to claim 21, wherein said pharmaceutical composition is a solid oral preparation, a liquid oral preparation, or an injection.

23. The compound according to claim 1, which is a crystalline form A of methyl (S,E)-2-(2-chlorophenyl)-2-(2-(2-pentenoyloxy)-6,7-dihydrothieno[3,2-c]pyridin-5(4H)-yl)-acetate (I-4), wherein said crystalline form A has an X-ray powder diffraction pattern having diffraction peaks at 5.32, 16.09, 18.28, 20.68 and 21.51 expressed by 2θ degree using Cu-Ka radiation, with a 2θ angle measurement error being ±0.2.

24. The crystal form A according to claim 23, characterized in that, said crystalline form A has an X-ray powder diffraction pattern having diffraction peaks at 5.32, 10.68, 12.98, 14.57, 16.09, 17.64, 18.28, 19.83, 20.68 and 21.51 expressed by 2θ degree using Cu-Ka radiation, with a 2θ angle measurement error being ±0.2.

25. A pharmaceutical composition comprising the crystalline form A of methyl (S,E)-2-(2-chlorophenyl)-2-(2-(2-pentenoyloxy)-6,7-dihydrothieno[3,2-c] pyridin-5(4H)-yl)-acetate (I-4) according to claim 23 and a pharmaceutically acceptable carrier or excipient.

26. The pharmaceutical composition according to claim 25, wherein said pharmaceutical composition is a solid oral preparation, a liquid oral preparation, or an injection.

27. The compound according to claim 1, which is a crystalline form A of methyl (S,E)-2-(2-chlorophenyl)-2-(2-(2-hexenoyloxy)-6,7-dihydrothieno[3,2-c]pyridin-5(4H)-yl)-acetate (I-5), wherein said crystalline form A has an X-ray powder diffraction pattern having diffraction peaks at 5.58, 16.84, 19.46, 22.50 and 23.47 expressed by 2θ degree using Cu-Ka radiation, with a 2θ angle measurement error being ±0.2.

28. The crystal form A according to claim 27, characterized in that, said crystalline form A has an X-ray powder diffraction pattern having diffraction peaks at 5.58, 11.19, 12.21, 15.64, 16.84, 19.00, 19.46, 20.09, 22.50, 23.47, 23.99 and 25.81 expressed by 2θ degree using Cu-Ka radiation, with a 2θ angle measurement error being ±0.2.

29. A pharmaceutical composition comprising the crystalline form A of methyl (S,E)-2-(2-chlorophenyl)-2-(2-(2-hexenoyloxy)-6,7-dihydrothieno[3,2-c] pyridin-5(4H)-yl)-acetate (I-5) according to claim 27 and a pharmaceutically acceptable carrier or excipient.

30. The pharmaceutical composition according to claim 29, wherein said pharmaceutical composition is a solid oral preparation, a liquid oral preparation, or an injection.

31. A method for preventing and/or treating cardiovascular and cerebrovascular diseases caused by platelet aggregation, the method comprises administering to a subject in need thereof a therapeutically effective amount of the compound according to claim 1.

32. A method for preventing and/or treating cardiovascular and cerebrovascular diseases caused by platelet aggregation, the method comprises administering to a subject in need thereof a therapeutically effective amount of the crystalline form A according to claim 7.

33. A method for preventing and/or treating cardiovascular and cerebrovascular diseases caused by platelet aggregation, the method comprises administering to a subject in need thereof a therapeutically effective amount of the crystalline form A according to claim 11.

34. A method for preventing and/or treating cardiovascular and cerebrovascular diseases caused by platelet aggregation, the method comprises administering to a subject in need thereof a therapeutically effective amount of the crystalline form B according to claim 15.

35. A method for preventing and/or treating cardiovascular and cerebrovascular diseases caused by platelet aggregation, the method comprises administering to a subject in need thereof a therapeutically effective amount of the crystalline form A according to claim 19.

36. A method for preventing and/or treating cardiovascular and cerebrovascular diseases caused by platelet aggregation, the method comprises administering to a subject in need thereof a therapeutically effective amount of the crystalline form A according to claim 23.

37. A method for preventing and/or treating cardiovascular and cerebrovascular diseases caused by platelet aggregation, the method comprises administering to a subject in need thereof a therapeutically effective amount of the crystalline form A according to claim 27.

\* \* \* \* \*

UNITED STATES PATENT AND TRADEMARK OFFICE
CERTIFICATE OF CORRECTION

PATENT NO. : 11,466,025 B2
APPLICATION NO. : 16/640612
DATED : October 11, 2022
INVENTOR(S) : C. Huang et al.

Page 1 of 1

It is certified that error appears in the above-identified patent and that said Letters Patent is hereby corrected as shown below:

In the Claims

| Column | Line | |
|---|---|---|
| 37 | 3 | In Claim 11, change "0.2." to -- ±0.2. --. |
| 37 | 26 | In Claim 15, change "0.2." to -- ±0.2. --. |

Signed and Sealed this
Fifth Day of November, 2024

Katherine Kelly Vidal
*Director of the United States Patent and Trademark Office*